US008263070B2

(12) United States Patent
Cherwinski et al.

(10) Patent No.: US 8,263,070 B2
(45) Date of Patent: Sep. 11, 2012

(54) METHODS OF MODULATING CD200 RECEPTORS

(75) Inventors: Holly M. Cherwinski, Boulder Creek, CA (US); Michael E. Bigler, Redwood City, CA (US); Jonathon D. Sedgwick, Palo Alto, CA (US); Joseph H. Phillips, Palo Alto, CA (US)

(73) Assignee: Schering Corporation, Kenilworth, NJ (US)

( * ) Notice: Subject to any disclaimer, the term of this patent is extended or adjusted under 35 U.S.C. 154(b) by 389 days.

(21) Appl. No.: 12/045,153

(22) Filed: Mar. 10, 2008

(65) Prior Publication Data

US 2008/0166353 A1 Jul. 10, 2008

Related U.S. Application Data

(63) Continuation of application No. 11/478,778, filed on Jun. 29, 2006, now abandoned, which is a continuation of application No. 10/389,231, filed on Mar. 13, 2003, now abandoned.

(60) Provisional application No. 60/364,513, filed on Mar. 15, 2002.

(51) Int. Cl.
*A61K 39/395* (2006.01)
(52) U.S. Cl. .................................................. 424/130.1
(58) Field of Classification Search ........................ None
See application file for complete search history.

(56) References Cited

U.S. PATENT DOCUMENTS

| 6,476,195 | B1 * | 11/2002 | Komatsoulis et al. ........ 530/350 |
| 7,186,818 | B2 * | 3/2007 | Van Der Vuurst De Vries et al. ............................. 536/23.5 |
| 2003/0077282 | A1 * | 4/2003 | Bigler et al. ................ 424/144.1 |
| 2004/0126777 | A1 * | 7/2004 | Bhatt et al. .......................... 435/6 |

FOREIGN PATENT DOCUMENTS

| WO | WO 00/70045 | 11/2000 |
| WO | WO 02/088164 A1 | 11/2002 |

OTHER PUBLICATIONS

Heaney et al., Lancet, 2005, 365: 974-976.*
Blazar et al., J. Immunol., 1996, 157: 3250-3259.*
Askenase, Philip W., et al., "Defective Elicitation of Delayed-Type Hypersensitivity in W/W and SI/SI Mast Cell-Deficient Mice", The Journal of Immunology, (Dec. 1983), pp. 2687-2694, vol. 131, No. 6.
Chen, Z., et al., "Cloning and characterization of the murine homologue of the rat/human MRC OX-2 gene", Biochim. Biophys. Acta, (1997), pp. 6/10, vol. 1362.
Dick, Andrew D., et al., "Distribution of IX2 Antigen and OX2 Receptor within Retina", Investigative Ophthalmology & visual Science, (Jan. 2001), pp. 170-176, vol. 42, No. 1.
Gorczynski, Reginald M., Evidence for an immunoregulatory Role of OX2 with its Counter Ligand (OX2L) in the Regulation of Transplant Rejection, Fetal Loss, Autoimmunity and Tumor Growth:, Archivum lmmunologiae et Therapiae Experimentalis, (2001), pp. 303-309, vol. 49.
Gorczynski, Reginald M., Transplant tolerance modifying antibody to CD200 receptor, but not CD200, alters cytokine production profile from stimulated macrophages:, Eur. J. Immunology, (2001), pp. 2331-2337, vol. 31.
Gorczynski, Reginald M., et al., "Synergy in induction of increased renal allograft survival after portal vein infusion of dendritic cells transduced to express TGFB and IL-10, along with administration of CHO cells expressing the regulatory molecule OX-2", Clinical Immunology, (Jun. 2000) pp. 182-189, vol. 95, No. 3.
Gorczynski, Reginald M., et al., "An Immunoadhesin Incorporating the Molecule OX-2 is a Potent Immunosuppressant that Prolongs Allo- and Xenograft Survival", The Journal of Immunology, (1999), 163: 1654-1660.
Gorczynski, Reginald M., et al., "Increased Expression of the Novel Molecule OX-2 is involved in Prolongation of Murine Renal Allograft Survival", Transplantation, (Apr. 27, 1998), pp. 1106-1114, vol. 65, No. 8.
Gorczynski, Reginald M., et al., "Evidence of a Role for CD200 in Regulation of Immune . Rejection of Leukaemic Tumor Cells in C57BL/6 Mice", Din. Exp. Immunology, (2001), pp. 220-229, vol. 126.
Gorczynski, Reginald M., et al., "CD200 Immunoadhesin Suppresses Collagen-induced Arthritis in Mice", Clinical Immunology, (Dec. 2001), pp. 328-334, vol. 101, No. 3.
Gorczynski, Reginald M., et al., "Evidence for Persistent Expression of OX2 as a Necessary Component of Prolonged Renal Allograft Survival Following Portal Vein immunization", (Oct. 2000), pp. 69-78, vol. 97. No. 1.
Gorczynski, Reginald M., et al., "Receptor Engagement of Cells Expressing a Ligand for the Tolerance-Inducing Molecule OX2 Induces an immunoregulatory Population That Inhibits Alloreactivity in Vitro and in Vivo", The Journal of Immunology, (2000), pp. 4854-4860, vol. 165.
Hoek, Robert M., et al., "Down-Regulation of the Macrophage Lineage Through Interaction with OX2 (CD200)", Science, (Dec. 1, 2000), pp. 1768-1771, vol. 290.
Black, Judith, "The Role of Mast Cells in the Pathophysiology of Asthma", New England Journal of Medicine, (May 30, 2002), pp. 1742-1743, vol. 346, No. 22.
Lanier, Lewis L., et al., "The ITAM-bearing Transmembrane adaptor DAP12 in lymphoid and myeloid cell function", Immunology Today, (Dec. 2000), pp. 611-614, vol. 21, No. 12.
Luross, Jeff A., et al., "The genetic and immunopathological process underlying collagen-induced arthritis", Immunology, (2001), 103:407-416.
Marone, Gianni, et al., Human mast cells and basophils in HIV-1 infection, Trends in Immunology, (May 2001), pp. 229-232, vol. 22, No. 5.
Muchamuel, Tony, et al., "IL-13 Protects Mice from Lipopolysaccharide-Induced Lethal Endotoxemia", The Journal of Immunology, (1997), pp. 2898-2903, vol. 158.

(Continued)

*Primary Examiner* — Ilia Ouspenski

(57) ABSTRACT

Provided are methods for modulating activity of the immune system using agonists or antagonists of a CD200 receptor. Also provided are methods of treatment and diagnosis of immune disorders.

7 Claims, 2 Drawing Sheets

OTHER PUBLICATIONS

Preston, Sandy, et al "The leukocyte/neuron cell surface antigen OX2 binds to a ligand on macrophages", European Journal of Immunology, (1997), pp. 1911-1918, vol. 27.

Ribatti, Domenico, et al., "The Role of Mast Cells in Tumor Angiogenesis", British Journal of Haematology, (2001), pp. 514-521, vol. 115.

Wright, G. J., et al., "The unusual distribution of the neuronal/lymphoid cell surface CD200 (OX2) glycoprotein is conserved in humans", Immunology, (2001), pp. 173-179, vol. 102.

Wright, Gavin J., et al "Lymphoid/Neuronal Cell Surface OX2 Glycoprotein Recognizes a Novel Receptor on Macrophages Implicated in the control of their Function", Immunity, (Aug. 2000), pp. 233-242, vol. 13.

* cited by examiner

SEQUENCE LISTING

```
<160> NUMBER OF SEQ ID NOS: 14

<210> SEQ ID NO 1
<211> LENGTH: 2255
<212> TYPE: DNA
<213> ORGANISM: Homo sapiens

<400> SEQUENCE: 1
cagagaaaag cttctgttcg tccaagttac taaccaggct aaaccacata gacgtgaagg      60
aaggggctag aaggaaggga gtgccccact gttgatgggg taagaggatc ctgtactgag     120
aagttgacca gagagggtct caccatgcgc acagttcctt ctgtaccagt gtggaggaaa     180
agtactgagt gaagggcaga aaaagagaaa acagaaatgc tctgcccttg gagaactgct     240
aacctagggc tactgttgat tttgactatc ttcttagtgg ccgaagcgga gggtgctgct     300
caaccaaaca actcattaat gctgcaaact agcaaggaga atcatgcttt agcttcaagc     360
agtttatgta tggatgaaaa acagattaca cagaactact cgaaagtact cgcagaagtt     420
aacacttcat ggcctgtaaa gatggctaca aatgctgtgc tttgttgccc tcctatcgca     480
```

```
ttaagaaatt tgatcataat aacatgggaa ataatcctga gaggccagcc ttcctgcaca      540
aaagcctaca ggaaagaaac aaatgagacc aaggaaacca actgtactga tgagagaata      600
acctgggtct ccagacctga tcagaattcg gaccttcaga ttcgtccagt ggccatcact      660
catgacgggt attacagatg cataatggta acacctgatg ggaatttcca tcgtggatat      720
cacctccaag tgttagttac acctgaagtg accctgtttc aaaacaggaa tagaactgca      780
gtatgcaagg cagttgcagg gaagccagct gcgcagatct cctggatccc agagggcgat      840
tgtgccacta gcaagaaata ctggagcaat ggcacagtga ctgttaagag tacatgccac      900
tgggaggtcc acaatgtgtc taccgtgacc tgccacgtct cccatttgac tggcaacaag      960
agtctgtaca tagagctact tcctgttcca ggtgccaaaa aatcagcaaa attatatatt     1020
ccatatatca tccttactat tattattttg accatcgtgg gattcatttg gttgttgaaa     1080
gtcaatggct gcagaaaata taaattgaat aaaacagaat ctactccagt tgttgaggag     1140
gatgaaatgc agcccatgc cagctacaca gagaagaaca atcctctcta tgatactaca     1200
aacaaggtga aggcatctca ggcattacaa agtgaagttg acacagacct ccatacttta     1260
taagttgttg gactctagta ccaagaaaca acaacaaacg agatacatta taattactgt     1320
ctgattttct tacagttcta gaatgaagac ttatattgaa attaggtttt ccaaggttct     1380
tagaagacat tttaatggat tctcattcat acccttgtat aattggaatt tttgattctt     1440
agctgctacc agctagttct ctgaagaact gatgttatta caaagaaaat acatgcccat     1500
gaccaaatat tcaaattgtg caggacagta ataatgaaa  accaaatttc ctcaagaaat     1560
aactgaagaa ggagcaagtg tgaacagttt cttgtgtatc ctttcagaat attttaatgt     1620
acatatgaca tgtgtatatg cctatggtat atgtgtcaat ttatgtgtcc ccttacatat     1680
acatgcacat atctttgtca aggcaccagt gggaacaata cactgcatta ctgttctata     1740
catatgaaaa cctaataata taagtcttag agatcatttt atatcatgac aagtagagct     1800
acctcattct ttttaatggt tatataaaat tccattgtat agttatatca ttatttaatt     1860
aaaaacaacc ctaatgatgg atatttagat tcttttaagt tttgtttatt tcttttaagt     1920
tttgtttgtg gtataaacaa taccacatag aatgtttctt gtgcatatat ctctttgttt     1980
ttgagtatat ctgtaggata actttcttga gtggaattgt caggtcaaag ggtttgtgca     2040
ttttactatt gatatatatg ttaaattgtg tcaaatatat atgtcaaatt ccctccaaca     2100
ttgtttaaat gtgcctttcc ctaaatttct attttaataa ctgtactatt cctgcttcta     2160
cagttgccac tttctctttt taatcaacca gattaaatat gatgtgagat tataataaga     2220
attatactat ttaataaaaa tggatttata ttttt                                2255
```

<210> SEQ ID NO 2
<211> LENGTH: 348
<212> TYPE: PRT
<213> ORGANISM: Homo sapiens

<400> SEQUENCE: 2

Met Leu Cys Pro Trp Arg Thr Ala Asn Leu Gly Leu Leu Leu Ile Leu
1               5                   10                  15

Thr Ile Phe Leu Val Ala Glu Ala Glu Gly Ala Ala Gln Pro Asn Asn
            20                  25                  30

Ser Leu Met Leu Gln Thr Ser Lys Glu Asn His Ala Leu Ala Ser Ser
        35                  40                  45

Ser Leu Cys Met Asp Glu Lys Gln Ile Thr Gln Asn Tyr Ser Lys Val
    50                  55                  60

| | | | | | | | | | | | | | | | |
|---|---|---|---|---|---|---|---|---|---|---|---|---|---|---|---|
|Leu|Ala|Glu|Val|Asn|Thr|Ser|Trp|Pro|Val|Lys|Met|Ala|Thr|Asn|Ala|
|65| | | |70| | | |75| | | |80| | | |

Val Leu Cys Cys Pro Pro Ile Ala Leu Arg Asn Leu Ile Ile Ile Thr
                         85                        90                        95

Trp Glu Ile Ile Leu Arg Gly Gln Pro Ser Cys Thr Lys Ala Tyr Arg
    100                          105                        110

Lys Glu Thr Asn Glu Thr Lys Glu Thr Asn Cys Thr Asp Glu Arg Ile
      115                        120                        125

Thr Trp Val Ser Arg Pro Asp Gln Asn Ser Asp Leu Gln Ile Arg Pro
    130                          135                        140

Val Ala Ile Thr His Asp Gly Tyr Tyr Arg Cys Ile Met Val Thr Pro
145                      150                        155                        160

Asp Gly Asn Phe His Arg Gly Tyr His Leu Gln Val Leu Val Thr Pro
                165                        170                        175

Glu Val Thr Leu Phe Gln Asn Arg Asn Arg Thr Ala Val Cys Lys Ala
            180                      185                        190

Val Ala Gly Lys Pro Ala Ala Gln Ile Ser Trp Ile Pro Glu Gly Asp
      195                        200                        205

Cys Ala Thr Lys Gln Glu Tyr Trp Ser Asn Gly Thr Val Thr Val Lys
    210                          215                        220

Ser Thr Cys His Trp Glu Val His Asn Val Ser Thr Val Thr Cys His
225                    230                        235                        240

Val Ser His Leu Thr Gly Asn Lys Ser Leu Tyr Ile Glu Leu Leu Pro
                245                        250                        255

Val Pro Gly Ala Lys Lys Ser Ala Lys Leu Tyr Ile Pro Tyr Ile Ile
            260                      265                        270

Leu Thr Ile Ile Ile Leu Thr Ile Val Gly Phe Ile Trp Leu Leu Lys
    275                          280                        285

Val Asn Gly Cys Arg Lys Tyr Lys Leu Asn Lys Thr Glu Ser Thr Pro
    290                          295                        300

Val Val Glu Glu Asp Glu Met Gln Pro Tyr Ala Ser Tyr Thr Glu Lys
305                    310                        315                        320

Asn Asn Pro Leu Tyr Asp Thr Thr Asn Lys Val Lys Ala Ser Gln Ala
                325                        330                        335

Leu Gln Ser Glu Val Asp Thr Asp Leu His Thr Leu
            340                      345

<210> SEQ ID NO 3
<211> LENGTH: 1010
<212> TYPE: DNA
<213> ORGANISM: Homo sapiens

<400> SEQUENCE: 3

```
atgggtggaa agcagatgac acagaactat tcaacaattt ttgcagaagg taacatttca      60
cagcctgtac tgatggatat aaatgctgtg ctttgttgcc tcctattgc attaagaaat     120 ttgatcataa taacatggga ataatcctg agaggccagc cttcctgcac aaaagcctac      180
aagaaagaaa caaatgagac caaggaaacc aactgtactg ttgagagaat aacctgggtc     240
tctagacctg atcagaattc ggaccttcag attcgtccgg tggacaccac tcatgacggg     300
tattacagag catagtggt aacacctgat gggaatttcc atcgtggata tcacctccaa      360
gtgttagtta cacccgaagt gaacctattt caaagcagga atataactgc agtatgcaag     420
gcagttacag ggaagccagc tgcccagatc tcctggatcc cagagggatc tattcttgcc     480
actaagcaag aatactgggg caatggcaca gtgacggtta agagtacatg cccctgggag     540
```

```
ggccacaagt ctactgtgac ctgccatgtc tcccatttga ctggcaacaa gagtctgtcc    600
gtaaagttga attcaggtct cagaacctca ggatctccag cgttgtcctt actgatcatt    660
ctttatgtga aactctctct ttttgtggtc attctggtca ccacaggatt tgttttcttc    720
cagaggataa atcatgtcag aaaagttctt taaagaagaa ggaagggtct tcttttgctt    780
ctcctccttg tctctggact gcaacattgg tgagatgagt gatggtccag cagtgaactt    840
gggccatgga tgatgttaag gatagaagcc actcagtagg atagaagaaa agaaagatgg    900
aagaaggatc ctgggcttga tgaccatgaa gtttccctat aaaccctcaa ccacctattc    960
attgacttct tttgtgttag agtgaataaa atttttgttca tgccagtgtt              1010
```

<210> SEQ ID NO 4
<211> LENGTH: 250
<212> TYPE: PRT
<213> ORGANISM: Homo sapiens

<400> SEQUENCE: 4

```
Met Gly Gly Lys Gln Met Thr Gln Asn Tyr Ser Thr Ile Phe Ala Glu
1               5                   10                  15

Gly Asn Ile Ser Gln Pro Val Leu Met Asp Ile Asn Ala Val Leu Cys
            20                  25                  30

Cys Pro Pro Ile Ala Leu Arg Asn Leu Ile Ile Thr Trp Glu Ile
        35                  40                  45

Ile Leu Arg Gly Gln Pro Ser Cys Thr Lys Ala Tyr Lys Lys Glu Thr
    50                  55                  60

Asn Glu Thr Lys Glu Thr Asn Cys Thr Val Glu Arg Ile Thr Trp Val
65                  70                  75                  80

Ser Arg Pro Asp Gln Asn Ser Asp Leu Gln Ile Arg Pro Val Asp Thr
                85                  90                  95

Thr His Asp Gly Tyr Tyr Arg Gly Ile Val Val Thr Pro Asp Gly Asn
            100                 105                 110

Phe His Arg Gly Tyr His Leu Gln Val Leu Val Thr Pro Glu Val Asn
        115                 120                 125

Leu Phe Gln Ser Arg Asn Ile Thr Ala Val Cys Lys Ala Val Thr Gly
    130                 135                 140

Lys Pro Ala Ala Gln Ile Ser Trp Ile Pro Glu Gly Ser Ile Leu Ala
145                 150                 155                 160

Thr Lys Gln Glu Tyr Trp Gly Asn Gly Thr Val Thr Val Lys Ser Thr
                165                 170                 175

Cys Pro Trp Glu Gly His Lys Ser Thr Val Thr Cys His Val Ser His
            180                 185                 190

Leu Thr Gly Asn Lys Ser Leu Ser Val Lys Leu Asn Ser Gly Leu Arg
        195                 200                 205

Thr Ser Gly Ser Pro Ala Leu Ser Leu Leu Ile Leu Tyr Val Lys
    210                 215                 220

Leu Ser Leu Phe Val Val Ile Leu Val Thr Thr Gly Phe Val Phe Phe
225                 230                 235                 240

Gln Arg Ile Asn His Val Arg Lys Val Leu
                245                 250
```

<210> SEQ ID NO 5
<211> LENGTH: 1624
<212> TYPE: DNA
<213> ORGANISM: Mus musculus

<400> SEQUENCE: 5

```
aaaaccgaaa tgttttgctt ttggagaact tctgccctag cagtgctctt aatatggggg      60
gtctttgtgg ctgggtcaag ttgtactgat aagaatcaaa caacacagaa caacagttca     120
tctcctctga cacaagtgaa cactacagtg tctgtacaga taggtacaaa ggctctgctc     180
tgctgctttt ctattccact gacaaaagca gtattaatca catggataat aaagctcaga     240
ggcctgccat cctgcacaat agcatacaaa gtagatacaa agaccaatga aaccagctgc     300
ttgggcagga acatcacctg gcctccaca cctgaccaca gtcctgaact tcagatcagt      360
gcagtgaccc tccagcatga ggggacttac acatgtgaga cagtaacacc tgaagggaat     420
tttgaaaaaa actatgacct ccaagtgctg gtgcccctg aagtaaccta ctttccagag      480
aaaaacagat ctgcagtctg tgaggcaatg caggcaagc ctgctgcaca gatctcttgg      540
tctccagatg gggactgtgt cactacgagt gaatcacaca gcaatggcac tgtgactgtc     600
aggagcacat gccactggga gcagaacaat gtgtctgatg tgtcctgcat tgtctctcat     660
ttgactggta accaatctct gtccatgaa ctgagtagag tggtaaccaa atcattacga      720
ccatatattc catacatcat accatcaatt atcattttga tcatcatagg atgcatttgt     780
cttttgaaaa tcagtggctt cagaaaatgc aaattgccaa aattagaagc tacttcagct     840
attgaggagg atgaaatgca gccttatgct agctatacag agaagagcaa tccactctat     900
gatactgtga ctaaggtgga ggcatttcca gtatcacaag cgaagtcaa tggcacagac      960
tgccttactt tgtcggccat tggaatctag aaccaagaaa aagaagtca agagacatca     1020
taattactgc tttgctttct ttaaaattcg acaatggaag gactacttgg aaattagctc     1080
ttccaaagct attaaaagc acaaatgttc taatgaaatt gcatttaaat tctatcattg     1140
gaagtttgga atctctgctg ctacctgtta atttaggaa gaactgattt aattattaca     1200
aagaaagcac atggttatgg tgaaatatca agttgtgcaa taaagtatga tgaaaactga     1260
gtttcctcaa gaaataactg caggaggaac aatcatcact aaagaatttc atgtgagttc     1320
ttacaaaaaa attcctatgt atacatgact atggtatgtg tgtccaatta catgtttatt     1380
tacaaatgtg tatatatgca cacatttgct tttcaggaca tctccttgta aaaacacac     1440
tggagttttg gatttataaa agcttataaa gtgagcattg gagatatttt tatatcagca     1500
taagtaaatc tacctcattc tttttaatgg ctacatagaa ttctcctgta tgattacatt     1560
gtaatttaat taatcatggc ccttggattt tgtgttgtgt gtggtattaa acaaaaccat     1620
gtag                                                                  1624
```

<210> SEQ ID NO 6
<211> LENGTH: 326
<212> TYPE: PRT
<213> ORGANISM: Mus musculus

<400> SEQUENCE: 6

```
Met Phe Cys Phe Trp Arg Thr Ser Ala Leu Ala Val Leu Leu Ile Trp
  1               5                  10                  15

Gly Val Phe Val Ala Gly Ser Ser Cys Thr Asp Lys Asn Gln Thr Thr
             20                  25                  30

Gln Asn Asn Ser Ser Ser Pro Leu Thr Gln Val Asn Thr Thr Val Ser
         35                  40                  45

Val Gln Ile Gly Thr Lys Ala Leu Leu Cys Cys Phe Ser Ile Pro Leu
     50                  55                  60

Thr Lys Ala Val Leu Ile Thr Trp Ile Ile Lys Leu Arg Gly Leu Pro
 65                  70                  75                  80
```

```
Ser Cys Thr Ile Ala Tyr Lys Val Asp Thr Lys Asn Glu Thr Ser
                85                  90                  95

Cys Leu Gly Arg Asn Ile Thr Trp Ala Ser Thr Pro Asp His Ser Pro
            100                 105                 110

Glu Leu Gln Ile Ser Ala Val Thr Leu Gln His Glu Gly Thr Tyr Thr
            115                 120                 125

Cys Glu Thr Val Thr Pro Glu Gly Asn Phe Glu Lys Asn Tyr Asp Leu
            130                 135                 140

Gln Val Leu Val Pro Pro Glu Val Thr Tyr Phe Pro Glu Lys Asn Arg
145                 150                 155                 160

Ser Ala Val Cys Glu Ala Met Ala Gly Lys Pro Ala Ala Gln Ile Ser
                165                 170                 175

Trp Ser Pro Asp Gly Asp Cys Val Thr Thr Ser Glu Ser His Ser Asn
            180                 185                 190

Gly Thr Val Thr Val Arg Ser Thr Cys His Trp Glu Gln Asn Asn Val
            195                 200                 205

Ser Asp Val Ser Cys Ile Val Ser His Leu Thr Gly Asn Gln Ser Leu
            210                 215                 220

Ser Ile Glu Leu Ser Arg Gly Gly Asn Gln Ser Leu Arg Pro Tyr Ile
225                 230                 235                 240

Pro Tyr Ile Ile Pro Ser Ile Ile Leu Ile Ile Ile Gly Cys Ile
                245                 250                 255

Cys Leu Leu Lys Ile Ser Gly Phe Arg Lys Cys Lys Leu Pro Lys Leu
            260                 265                 270

Glu Ala Thr Ser Ala Ile Glu Glu Asp Glu Met Gln Pro Tyr Ala Ser
            275                 280                 285

Tyr Thr Glu Lys Ser Asn Pro Leu Tyr Asp Thr Val Thr Lys Val Glu
290                 295                 300

Ala Phe Pro Val Ser Gln Gly Glu Val Asn Gly Thr Asp Cys Leu Thr
305                 310                 315                 320

Leu Ser Ala Ile Gly Ile
                325

<210> SEQ ID NO 7
<211> LENGTH: 1386
<212> TYPE: DNA
<213> ORGANISM: Mus musculus

<400> SEQUENCE: 7
agaggccagc cttcctgcat aatggcctac aaagtagaaa caaaggagac caatgaaacc        60
tgcttgggca ggaacatcac ctgggcctcc acacctgacc acattcctga ccttcagatc       120
agtgcggtgg ccctccagca tgaggggaat tacttatgtg agataacaac acctgaaggg       180
aatttccata agtctatgaa cctccaagtg ctggtgcccc tgaagtaac ctactttctc        240 ggggaaaata gaactgcagt tgtgaggca atggcaggca agcctgctgc acagatctct        300
tggactccag atggggactg tgtcactaag agtgagtcac acagcaatgg cactgtgact       360
gtcaggagca cttgccactg ggagcagaac aatgtgtctg ctgtgtcctg cattgtctct       420
cattcgactg gtaatcagtc tctgtccata gaactgagta gaggtaccac cagcaccacc       480
ccttccttgc tgaccattct ctacgtgaaa atgtcctttt ggggattat tcttcttaaa        540 gtgggatttg ctttcttcca gaagagaaat gttaccagaa catgaatatc agatttctg       600 gaagctcatt agtctgatga cacataccag aaaacagcat tgtaatcaa ctttctcatt        660 ggaatccagc ttacccgtcc ctgctgtctt catgtttgtt agacactcac ctccaaattc       720
```

| | |
|---|---|
| ttaactgaga agggctcctg tctaaaggaa atatggggac aaattgtgga gcatagacca | 780 |
| aaagaaaggc catccagaga ctgccccacc taaggaccca tcccatatac agacaccaaa | 840 |
| cccagacact actgaagatg ctgcgaagcg tttgctgaca ggagcctgtt atagctgtct | 900 |
| cctgagaggc tcagccagag cctgacaaat acataggtag atgcttgcag ccaacaactg | 960 |
| gactgagcaa aaatctcca ttggaggagt tagagaaagg actgaagagg gtgaaagggt | 1020 |
| ttgcagcccc ataggaagaa caacaatatc aaccaaccag atctcccaga gctcccaggg | 1080 |
| actaaattac caaccaaagg ctacacatgg aaggacctat ggctccagct gcttgtgtag | 1140 |
| cagtggatgg ccttgttggg catcagtgga aggagaaacc cttggtccag taaaggcttg | 1200 |
| attccctagt gtaagagaat gccagggcag tgacgtggga gtgagtaggt aggaagcatc | 1260 |
| ctcatagatg caggagaaag gagaatggaa gagggtattc tggagggaa actgaaaaag | 1320 |
| gagacaacat ttgaaatgta aatacataaa atatccaata aaaaatgtac agttgccagt | 1380 |
| catgtg | 1386 |

<210> SEQ ID NO 8
<211> LENGTH: 194
<212> TYPE: PRT
<213> ORGANISM: Mus musculus

<400> SEQUENCE: 8

```
Arg Gly Gln Pro Ser Cys Ile Met Ala Tyr Lys Val Glu Thr Lys Glu
1               5                   10                  15

Thr Asn Glu Thr Cys Leu Gly Arg Asn Ile Thr Trp Ala Ser Thr Pro
            20                  25                  30

Asp His Ile Pro Asp Leu Gln Ile Ser Ala Val Ala Leu Gln His Glu
        35                  40                  45

Gly Asn Tyr Leu Cys Glu Ile Thr Thr Pro Glu Gly Asn Phe His Lys
    50                  55                  60

Val Tyr Asp Leu Gln Val Leu Val Pro Pro Glu Val Thr Tyr Phe Leu
65                  70                  75                  80

Gly Glu Asn Arg Thr Ala Val Cys Glu Ala Met Ala Gly Lys Pro Ala
                85                  90                  95

Ala Gln Ile Ser Trp Thr Pro Asp Gly Asp Cys Val Thr Lys Ser Glu
            100                 105                 110

Ser His Ser Asn Gly Thr Val Thr Val Arg Ser Thr Cys His Trp Glu
        115                 120                 125

Gln Asn Asn Val Ser Ala Val Ser Cys Ile Val Ser His Ser Thr Gly
    130                 135                 140

Asn Gln Ser Leu Ser Ile Glu Leu Ser Arg Gly Thr Thr Ser Thr Thr
145                 150                 155                 160

Pro Ser Leu Leu Thr Ile Leu Tyr Val Lys Met Val Leu Leu Gly Ile
                165                 170                 175

Ile Leu Leu Lys Val Gly Phe Ala Phe Phe Gln Lys Arg Asn Val Thr
            180                 185                 190

Arg Thr
```

<210> SEQ ID NO 9
<211> LENGTH: 1354
<212> TYPE: DNA
<213> ORGANISM: Mus musculus

<400> SEQUENCE: 9

| | |
|---|---|
| ggcacgagtt acgatttgtg cttaacctga ctccactcca gatgcatgct ttggggagga | 60 |

```
ctctggcttt gatgttactc atcttcatca ctattttggt gcctgagtca agttgttcag    120
tgaaaggacg ggaggagatc ccaccggatg attcatttcc tttttcagat gataatatct    180
tccctgatgg agtgggcgtc accatggaga ttgagattat cactccagtg tctgtacaga    240
taggtatcaa ggctcagctt ttctgtcatc ctagtccatc aaaagaagca acacttagaa    300
tatgggaaat aactcccaga gactggcctt cctgcagact accctacaga gcagagttgc    360
agcagatcag taaaaaaatc tgtactgaga gaggaaccac tagggtccct gcacatcacc    420
agagttctga ccttcccatc aaatcaatgg ccctcaagca tgatgggcat tactcatgtc    480
ggatagaaac aacagatggg attttccaag agagacatag catccaagtg ccaggggaaa    540
atagaactgt agtttgtgag gcaattgcaa gcaagcctgc tatgcagatc ttgtggactc    600
cagatgagga ctgtgtcact aagagtaaat cacacaatga caccatgatt gtcaggagca    660
agtgccacag ggagaaaaac aatggccaca gtgtgttctg ctttatctcc catttgactg    720
ataactggat tctctccatg aacagaatcg gaggtacaac cagcatcctg ccttccttgc    780
tgagcattct ctatgtgaaa ctggctgtaa ctgttctcat cgtaggattt gcttttttcc    840
agaagagaaa ttatttcaga gtgccagaag gctcctgagg agagtggtct gtggttaaga    900
tgagatttac caccatctga agacatcttt gtctaccgcg cagcgtgctg agattccgag    960
aagcagccac agaacctact aggaagacaa atctgatgtg ttgtcaatcc tttcaatgg    1020 acctgagtac ttctataaac ccgagtgagg ttgtgctgga cccaggagcc aggctaggtc    1080
atatatgttg atttttgctg caagacctca tggtttatct acaaatccta aattctttca    1140
cttccagttt taaaacttttt ggcccaagca ttttatccac agcataacac ctttaaagaa    1200
actctcccac ggaaactgct ggttccatgg aatggaaaat tgcaacatgg tttacaagac    1260
agtgcaaacc aagcagcatt ccaagatatg agcttcagaa agttacagga actgtcttgg    1320
gacgagaaag aaggattaaa tagttcccag tccc                                1354
```

<210> SEQ ID NO 10
<211> LENGTH: 278
<212> TYPE: PRT
<213> ORGANISM: Mus musculus

<400> SEQUENCE: 10

```
Met His Ala Leu Gly Arg Thr Leu Ala Leu Met Leu Leu Ile Phe Ile
1               5                   10                  15

Thr Ile Leu Val Pro Glu Ser Ser Cys Ser Val Lys Gly Arg Glu Glu
            20                  25                  30

Ile Pro Pro Asp Asp Ser Phe Pro Phe Ser Asp Asp Asn Ile Phe Pro
        35                  40                  45

Asp Gly Val Gly Val Thr Met Glu Ile Glu Ile Thr Pro Val Ser
    50                  55                  60

Val Gln Ile Gly Ile Lys Ala Gln Leu Phe Cys His Pro Ser Pro Ser
65                  70                  75                  80

Lys Glu Ala Thr Leu Arg Ile Trp Glu Ile Thr Pro Arg Asp Trp Pro
                85                  90                  95

Ser Cys Arg Leu Pro Tyr Arg Ala Glu Leu Gln Gln Ile Ser Lys Lys
            100                 105                 110

Ile Cys Thr Glu Arg Gly Thr Thr Arg Val Pro Ala His His Gln Ser
        115                 120                 125

Ser Asp Leu Pro Ile Lys Ser Met Ala Leu Lys His Asp Gly His Tyr
    130                 135                 140

Ser Cys Arg Ile Glu Thr Thr Asp Gly Ile Phe Gln Glu Arg His Ser
```

```
                145                 150                 155                 160
Ile Gln Val Pro Gly Glu Asn Arg Thr Val Val Cys Glu Ala Ile Ala
                    165                 170                 175

Ser Lys Pro Ala Met Gln Ile Leu Trp Thr Pro Asp Glu Asp Cys Val
                180                 185                 190

Thr Lys Ser Lys Ser His Asn Asp Thr Met Ile Val Arg Ser Lys Cys
                195                 200                 205

His Arg Glu Lys Asn Asn Gly His Ser Val Phe Cys Phe Ile Ser His
            210                 215                 220

Leu Thr Asp Asn Trp Ile Leu Ser Met Glu Gln Asn Arg Gly Thr Thr
225                 230                 235                 240

Ser Ile Leu Pro Ser Leu Leu Ser Ile Leu Tyr Val Lys Leu Ala Val
                245                 250                 255

Thr Val Leu Ile Val Gly Phe Ala Phe Phe Gln Lys Arg Asn Tyr Phe
                260                 265                 270

Arg Val Pro Glu Gly Ser
            275

<210> SEQ ID NO 11
<211> LENGTH: 813
<212> TYPE: DNA
<213> ORGANISM: Mus musculus

<400> SEQUENCE: 11
atgcatgctc tggggaggat tccgactttg actttgctga tcttcatcaa tatttttgtg      60
tctgggtcaa gttgtactga tgagaatcaa acaatacaga atgacagttc atcttctctg     120
acacaagtta acactacaat gtctgtacag atggataaaa aggctctgct ctgctgcttt     180
tctagtccac tgataaatgc agtattaatc acatggataa taaaacacag acacctgcct     240
tcctgcacaa tagcatacaa cctagataaa aagaccaatg aaaccagctg cttgggcagg     300
aacatcacct gggcctccac acctgaccac agtcctgaac ttcagatcag tgcagtggcc     360
ctccagcatg aggggactta cacatgtgag atagtaacac ctgaagggaa tttagaaaaa     420
gtctatgacc tccaagtgct ggtgcccccct gaggtaacct actttccagg gaaaaacaga     480
actgcagtct gtgaggcaat ggcaggcaag cctgctgcac agatctcttg gactccagat     540
ggggactgtg tcactaagag tgagtcacac agcaatggca ctgtgactgt caggagcacg     600
tgccactggg agcagaacaa tgtgtctgtt gtgtcctgct agtctctca ttcgactggt     660 aatcagtctc tgtccataga actgagtcaa ggtacaatga ccacccccccg ttccttgctg     720 accattctct atgtgaaaat ggcccttttg gtgattattc ttcttaacgt aggatttgct     780
ttcttccaga agagaaattt tgccagaaca tga                                   813

<210> SEQ ID NO 12
<211> LENGTH: 270
<212> TYPE: PRT
<213> ORGANISM: Mus musculus

<400> SEQUENCE: 12

Met His Ala Leu Gly Arg Ile Pro Thr Leu Thr Leu Leu Ile Phe Ile
1               5                   10                  15

Asn Ile Phe Val Ser Gly Ser Ser Cys Thr Asp Glu Asn Gln Thr Ile
                20                  25                  30

Gln Asn Asp Ser Ser Ser Ser Leu Thr Gln Val Asn Thr Thr Met Ser
            35                  40                  45

Val Gln Met Asp Lys Lys Ala Leu Leu Cys Cys Phe Ser Ser Pro Leu
```

```
            50                  55                  60
Ile Asn Ala Val Leu Ile Thr Trp Ile Ile Lys His Arg His Leu Pro
 65                  70                  75                  80

Ser Cys Thr Ile Ala Tyr Asn Leu Asp Lys Lys Thr Asn Glu Thr Ser
                 85                  90                  95

Cys Leu Gly Arg Asn Ile Thr Trp Ala Ser Thr Pro Asp His Ser Pro
                100                 105                 110

Glu Leu Gln Ile Ser Ala Val Ala Leu Gln His Glu Gly Thr Tyr Thr
            115                 120                 125

Cys Glu Ile Val Thr Pro Glu Gly Asn Leu Glu Lys Val Tyr Asp Leu
        130                 135                 140

Gln Val Leu Val Pro Pro Glu Val Thr Tyr Phe Pro Gly Lys Asn Arg
145                 150                 155                 160

Thr Ala Val Cys Glu Ala Met Ala Gly Lys Pro Ala Ala Gln Ile Ser
                165                 170                 175

Trp Thr Pro Asp Gly Asp Cys Val Thr Lys Ser Glu Ser His Ser Asn
            180                 185                 190

Gly Thr Val Thr Val Arg Ser Thr Cys His Trp Glu Gln Asn Asn Val
        195                 200                 205

Ser Val Val Ser Cys Leu Val Ser His Ser Thr Gly Asn Gln Ser Leu
    210                 215                 220

Ser Ile Glu Leu Ser Gln Gly Thr Met Thr Thr Pro Arg Ser Leu Leu
225                 230                 235                 240

Thr Ile Leu Tyr Val Lys Met Ala Leu Leu Val Ile Ile Leu Leu Asn
                245                 250                 255

Val Gly Phe Ala Phe Phe Gln Lys Arg Asn Phe Ala Arg Thr
            260                 265                 270

<210> SEQ ID NO 13
<211> LENGTH: 2358
<212> TYPE: DNA
<213> ORGANISM: Rattus sp.

<400> SEQUENCE: 13
agcggaggga tcctggtcat ggtcaccgct gctcccctac ctgtgaagag aaagagcacc     60
gagtgagccg ctgaaaacca gaaaaccgaa atgctctgct tttggagaac ttctcacgta    120
gcagtactct tgatctgggg ggtcttcgcg gctgagtcaa gttgtcctga taagaatcaa    180
acaatgcaga acaattcatc aactatgaca gaagttaaca ctacagtgtt tgtacagatg    240
ggtaaaaagg ctctgctctg ctgcccttct atttcactga caaagtaat attaataaca    300 tggacaataa ccctcagagg acagccttcc tgcataatat cctacaaagc agacacaagg    360
gagacccatg aaagcaactg ctcggacaga agcatcacct gggcctccac acctgacctc    420
gctcctgacc ttcagatcag tgcagtggcc ctccagcatg aagggcgtta ctcatgtgat    480
atagcagtac ctgacgggaa tttccaaaac atctatgacc tccaagtgct ggtgccccct    540
gaagtaaccc actttccagg ggaaaataga actgcagttt gtgaggcgat gcaggcaaa    600 cctgctgcgc agatctcttg gacgccagat ggggattgtg tcgctaagaa tgaatcacac    660
agcaatggca ccgtgactgt ccggagcaca tgccactggg agcagagcca cgtgtctgtc    720
gtgttctgtg ttgtctctca cttgacaact ggtaaccagt ctctgtctat agaactgggt    780
agagggggtg accaattatt aggatcatac attcaataca tcatcccatc tattattatt    840
ttgatcatca taggatgcat ttgtcttttg aaaatcagtg ctgcagaaa atgtaaattg    900 ccaaaatcgg gagctactcc agatattgag gaggatgaaa tgcagccgta tgctagctac    960
```

```
acagagaaga gcaatccact ctatgatact gtgaccacga cggaggcaca cccagcgtca   1020
caaggcaaag tcaatggcac agactgtctt actttgtcag ccatgggaat ctagaaccaa   1080
ggaaaagaag tcaagagaca tcataattac tgcttttctt tctttaaact tctccaatgg   1140
agggaaatta gctcttctga agttcttaga aagcacaaat gttctaatgg atttgccttt   1200
aagttcttct atcattggaa gtttggaatc tttgctgcta cctgttaatt ctaggaagaa   1260
ctgatttaat tattacaaag aaagcacatt gttatggtaa aatatcaaat tgtgcaatac   1320
aatgatgaaa actgagtttc ctcaagaaat aactgcagaa ggaacaatca ttactaaagc   1380
atttcatgtg agttcttcca aaaagaaaa tccctgtgta tacgacatga ttatggtatg    1440
tgtgtgcctt tatatgtttg tttacaaatg tgtatatatg cacacatctg attatcaaga   1500
catctctgtc aaaaactcac tggcgttcca gatttatgaa agctaataaa gtgagtattg   1560
gagatgtttt tatatctgta tatgtaaaac tacctcattc ttttttaatgg ctacataaaa  1620 ttcatggtcc ttggatgggc atttagactt tgtgttgtat gtggtattaa atgataccat   1680
gtggaatgtt tcttgtggtg aatctccgca ttatttgagt gcacctgtga gataatttct   1740
gtgagtgtaa tggtcctgtc agttggaatg cgcttttatg atcaatagat tagtcaaact   1800
gtgtcagttt acattttctc taattgtgtt taatgtgact ttctccatat tcttattctt   1860 atgttttttaa tatcttcact ttcacctttt atactttcca tctttaatta accagttggg  1920
tgatgtgtct taaggttgtg atattaactt tattatttaa tggaactgga ttcatatctt   1980
tgggtttcat gtccacaaaa gagatagaaa gcatttgtaa agacagtatt ttcaactcct   2040
tgtattacta caaaaatgtt gacatctgat gcacaacagt tttatggatg ttatgaattg   2100
tgtgttttta acattctatt ctgatgtact tataagagag caactgtctt tgaactatat   2160
atgtaggtgg gagaacttgg agtactttat gtgctaatag gatggtaatg ggatgatata   2220
acttttccct ccagtttttt ggagggaaat attaggaata catgtattga taattttag    2280 catatatttt ttaattgtta aaaataaacc tgttcccttt atatcaggaa agatattaaa   2340
aatggattta ttcatctc                                                 2358
```

<210> SEQ ID NO 14
<211> LENGTH: 327
<212> TYPE: PRT
<213> ORGANISM: Rattus sp.

<400> SEQUENCE: 14

```
Met Leu Cys Phe Trp Arg Thr Ser His Val Ala Val Leu Leu Ile Trp
1               5                   10                  15

Gly Val Phe Ala Ala Glu Ser Ser Cys Pro Asp Lys Asn Gln Thr Met
            20                  25                  30

Gln Asn Asn Ser Ser Thr Met Thr Glu Val Asn Thr Val Phe Val
        35                  40                  45

Gln Met Gly Lys Lys Ala Leu Leu Cys Cys Pro Ser Ile Ser Leu Thr
    50                  55                  60

Lys Val Ile Leu Ile Thr Trp Thr Ile Thr Leu Arg Gly Gln Pro Ser
65                  70                  75                  80

Cys Ile Ile Ser Tyr Lys Ala Asp Thr Arg Glu Thr His Glu Ser Asn
                85                  90                  95

Cys Ser Asp Arg Ser Ile Thr Trp Ala Ser Thr Pro Asp Leu Ala Pro
            100                 105                 110

Asp Leu Gln Ile Ser Ala Val Ala Leu Gln His Glu Gly Arg Tyr Ser
        115                 120                 125
```

```
Cys Asp Ile Ala Val Pro Asp Gly Asn Phe Gln Asn Ile Tyr Asp Leu
    130                 135                 140
Gln Val Leu Val Pro Pro Glu Val Thr His Phe Pro Gly Glu Asn Arg
145                 150                 155                 160
Thr Ala Val Cys Glu Ala Ile Ala Gly Lys Pro Ala Ala Gln Ile Ser
                165                 170                 175
Trp Thr Pro Asp Gly Asp Cys Val Ala Lys Asn Glu Ser His Ser Asn
            180                 185                 190
Gly Thr Val Thr Val Arg Ser Thr Cys His Trp Glu Gln Ser His Val
        195                 200                 205
Ser Val Val Phe Cys Val Val Ser His Leu Thr Thr Gly Asn Gln Ser
    210                 215                 220
Leu Ser Ile Glu Leu Gly Arg Gly Gly Asp Gln Leu Leu Gly Ser Tyr
225                 230                 235                 240
Ile Gln Tyr Ile Ile Pro Ser Ile Ile Ile Leu Ile Ile Ile Gly Cys
                245                 250                 255
Ile Cys Leu Leu Lys Ile Ser Gly Cys Arg Lys Cys Lys Leu Pro Lys
            260                 265                 270
Ser Gly Ala Thr Pro Asp Ile Glu Glu Asp Glu Met Gln Pro Tyr Ala
        275                 280                 285
Ser Tyr Thr Glu Lys Ser Asn Pro Leu Tyr Asp Thr Val Thr Thr Thr
    290                 295                 300
Glu Ala His Pro Ala Ser Gln Gly Lys Val Asn Gly Thr Asp Cys Leu
305                 310                 315                 320
Thr Leu Ser Ala Met Gly Ile
                325
```

METHODS OF MODULATING CD200 RECEPTORS

CROSS-REFERENCE TO RELATED APPLICATION

This application is a continuation application of U.S. Ser. No. 11/478,778 filed on Jun. 29, 2006, which is a continuation of U.S. Ser. No. 10/389,231 filed Mar. 13, 2003, which claims benefit of priority under 35 U.S.C 119(e) of U.S. Ser. No. 60/364,513 filed Mar. 15, 2002, the disclosures of which are hereby incorporated by reference in their entirety

FIELD OF THE INVENTION

The present invention relates to methods and compositions for modulating mammalian physiology, including immune system function. In particular, it provides methods for modulating the metabolism and activity of mast cells. Diagnostic and therapeutic uses are disclosed.

BACKGROUND OF THE INVENTION

The immune system, composed of cells of the bone marrow, spleen, and hematopoietic cells, including but not limited to lymphoid and myeloid lineage cells, is responsible for defending against bacteria, viruses, and foreign multicellular organisms, as well as cancer cells. Improper regulation of the immune system can result in a number of disorders or pathological conditions, e.g., chronic inflammation, autoimmune diseases and disorders, and undesired allergic reactions to foreign particles or foreign tissues.

Mast cells, a myeloid lineage immune cell, secrete a variety of cytokines and enzymes that result in inflammation. As some of these substances occur in secretory vesicles that appear granular, the process of secretion is sometimes called degranulation. Rapid degranulation by mast cells contributes to the pathology of asthma, anaphylaxis, and other allergic responses, while slower degranulation by mast cells contributes to arthritis and other types of chronic inflammation. The release of inflammatory cytokines and enzymes by mast cells can result in tissue damage, further attraction of mast cells, resulting in further tissue damage.

Cells of the immune system possess many types of membrane-bound proteins that can serve as receptors. The ligands for these receptors can be small molecules, proteins, e.g. cytokines or chemokines, or membrane-bound proteins residing on a separate cell. Changes in the activity of a cell or tissue can result from occupation of a receptor by its physiological ligand, by an analogue of the physiological ligand, by an antibody, by agents that cross-link like-receptors to each other, and by agents that cross-link non-identical receptors to each other.

Mast cells contain a number of receptors that relay an inhibitory signal to the dell. These include CD200 receptor a (a.k.a. CD200Ra; OX2Ra), as well as various Ig-ITIM-bearing receptors, e.g., low affinity IgG receptor FcγRIIB, transmembrane glycoprotein receptor gp49B1, signal regulatory protein (SIRP), mast cell function-associated Ag, and platelet endothelial cell adhesion molecule-1 (PECAM-1)/(CD31) (Wong, et al. (2002) *J. Immunol.* 168:6455-6462).

CD200 (a.k.a. OX2) is a widely distributed membrane-bound protein occurring on lymphoid, neuronal, endothelial, dendritic cells, and B cells (Wright et al. (2000) *Immunity* 13, 233-242; Wright, et al. (2001) *Immunology* 102:173-179; Hoek, et al. (2000) *Science* 290:1768-1771; Barclay, et al. (2001) *Immunol.* 102:173-179; McCaughan, et al. (1987) *Immunogenetics* 25:329-335). CD200, the ligand of CD200R, can bind to CD200R, which is expressed on a separate cell. In humans, two subtypes of CD200Rs have been identified, hCD200Ra (SEQ ID NO:2) and hCD200Rb (SEQ ID NO:4). Murine homologs of CD200R consist of four receptor subtypes, CD200Ra (SEQ ID NO:6), CD200Rb (SEQ ID NO:8), CD200Rc (SEQ ID NO:10), and CD200Rd (SEQ ID NO:12). CD200Ra occurs, e.g., on macrophages, dendritic cells, and microglia, of the rat (Wright, et al. (2000) supra; Preston, et al. (1997) *Eur. J. Immunol.* 27:1911-1918.

Several regulatory pathways involving the membrane bound proteins for various immune cells have been identified. However, the molecules responsible for mast cell regulation are poorly understood. The present invention fulfills this need by providing methods of diagnosis and treatment of mast cell disorders by targeting mast cell receptor molecules, e.g., CD200Rs.

SUMMARY OF THE INVENTION

Figure 1:
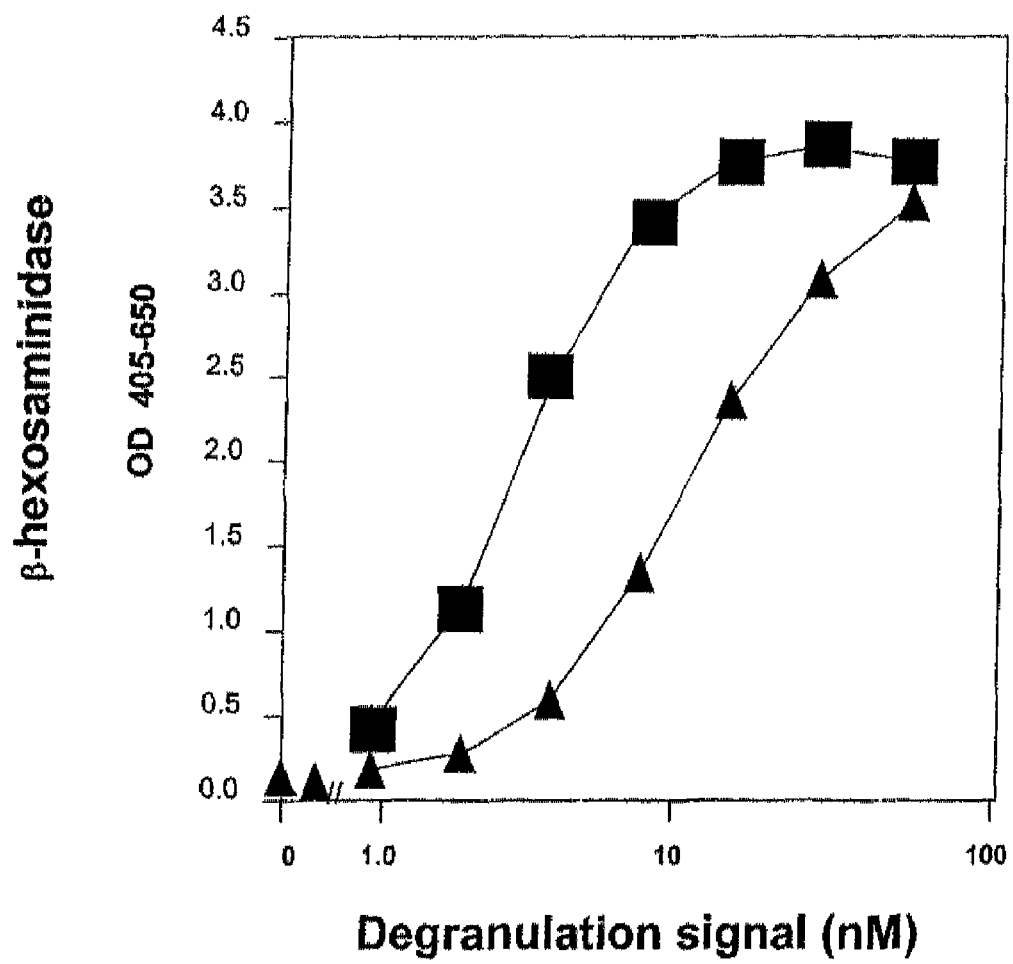
FIG. 1 shows secretion of β-hexosaminidase versus concentration of degranulation signal.

The invention is based, in part, upon the discovery that binding of an antibody to an inhibiting receptor, e.g., CD200Ra, inactivates a cell.

The invention provides a method of modulating the activity of a cell comprising contacting the cell with a binding composition derived from the antigen binding site of an antibody that specifically binds to CD200Ra (SEQ ID NOs:2 or 6), or an antigenic fragment thereof. Also provided is the above method wherein the cell is a mast cell; wherein the modulating inhibits cell activity or stimulates cell activity; wherein the modulating inhibits cell activity and the binding composition comprises an agonist of CD200Ra (SEQ ID NOs:2 or 6); or wherein the modulating increases cell activity and the binding composition comprises an antagonist of CD200Ra (SEQ ID NOs.2 or 6). In another embodiment, the invention provides the above method wherein the binding composition comprises a humanized antibody; a monoclonal antibody; a polyclonal antibody; an Flab fragment; an F(ab')$_2$ fragment; a peptide mimetic of an antibody; or a detectable label. Yet another aspect of the invention is the above method, farther comprising contacting the cell with an agent that specifically enhances expression of CD200Ra (SEQ ID NOs:2 or 6).

Also encompassed is a method of treating a subject suffering from an immune condition comprising treating with or administering the binding composition derived from the antigen binding site of an antibody that specifically binds to CD200Ra (SEQ ID NOs:2 or 6), or an antigenic fragment thereof. Also provided is the above method, wherein the binding composition comprises an agonist or antagonist of CD200Ra (SEQ ID NOs:2 or 6); wherein the immune condition is an inflammatory condition or an autoimmune condition. Also contemplated is the above method wherein the immune condition is rheumatoid arthritis; endotoxcemia; psoriasis; or allergy; or where the immune condition is an infection or a cancerous condition. Further contemplated is the above method wherein the binding composition is administered in conjunction with an agent that specifically enhances expression CD200Ra (SEQ ID NOs:2 or 6), or an antigenic fragment hereof.

DETAILED DESCRIPTION

As used herein, including the appended claims, the singular forms of words such as "a," "an," and "the" include their corresponding plural references unless the context clearly dictates otherwise.

I. DEFINITIONS

"Activity" of a molecule may describe or refer to binding of the molecule to a ligand or to a receptor, to catalytic activity, to the ability to stimulate gene expression, to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" may also mean specific activity, e.g., [catalytic activity]/[mg protein], or [immunological activity]/[mg protein], or the like.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, including selenomethionine, as well as those amino acids that are modified after incorporation into a polypeptide, e.g., hydroxyproline, O-phosphoserine, O-phosphotyrosine, γ-carboxyglutainate, and cystine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetic refers to a chemical compound that has a structure that is different from the general chemical structure of an amino acid, but that unctions in a manner similar to a naturally occurring amino acid. Amino acids may be referred to herein by either their commonly known three letter symbols or by their one-letter symbols.

"Binding composition" encompasses, e.g., an antibody, polyclonal antibody, monoclonal antibody, engineered antibody, recombinant antibody, humanized antibody, binding fragment derived from an antibody, peptide mimetic of an antibody, a bifunctional, or multifunctional reagent. The binding composition may further comprise, e.g., a linker, oligosaccharide, or label. "Derived from an antibody" refers, e.g., to treatment or manipulation of an antibody to produce a fragment or complex, e.g., an antigen-binding site of the antibody, or use of genetically engineering to produce a molecule or complex that mimics predetermined features of the antibody, e.g., the antigen binding site.

"Bispecific antibody" generally refers to a covalent complex, but may refer to a stable non-covalent complex of binding fragments from two different antibodies, humanized binding fragments from two different antibodies, or peptide mimetics of binding fragments from two different antibodies. Each binding fragment recognizes a different target or epitope, e.g., a different receptor, e.g., an inhibiting receptor and an activating receptor. Bispecific antibodies normally exhibit specific binding to two different antigens.

"Conservatively modified variants" applies to both amino acid and nucleic acid sequences. With respect to particular nucleic acid sequences, conservatively modified variant refers to those nucleic acids that encode identical or essentially identical amino acid sequences. An example of a conservative substitution is the exchange of an amino acid in one of the following groups for another amino acid of the same group (U.S. Pat. No. 5,767,063 issued to Lee, et al.; Kyte and Doolittle (1982) *J. Mol. Biol.* 157:105-132).

(1) Hydrophobic: Norleucine, Ile, Val, Leu, Phe, Cys, Met;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro;
(6) Aromatic: Trp, Tyr, Phe; and
(7) Small amino acids: Gly, Ala, Ser.

Methods relating to polypeptide molecules having substantially the same amino acid sequence as CD200 or CD200R (SEQ ID. NOs:2, 4, 6, 8, 10, 12) but possessing minor amino acid substitutions, truncations, or deletions, that do not substantially affect the functional aspects are within the definition of the contemplated invention. Variants containing one or more peptide bond cleavages, where daughter polypeptides remain in association with each other, are within the definition of the contemplated invention.

"ITIM" and "ITAM" are two motifs found on some inhibiting and activating receptors, respectively. The ITIM motif is defined by the consensus sequence I/V/LxYxxL/V in the cytoplasmic domain where (Y) can be phosphorylated, resulting in the ability of the polypeptide bearing the ITIM motif to recruit various enzymes, where the enzymes aid in relaying an inhibitory signal to the cell (Sathish, et al., (2001) *J. Immunol.* 166:1763-1770). The consensus ITAM sequence is $YxxL/Ix_{6-8}YxxX/I$, where (Y) may be phosphorylated resulting in a change in signaling properties of the activating receptor or an accessory protein. The ITAM motif may occur within an activating receptor itself, or within an accessory protein that binds to the activating receptor, thus conferring activating properties to the activating receptor.

"Monofunctional reagent" refers, e.g., to an antibody, binding composition derived from the binding site of an antibody, an antibody mimetic, a soluble receptor, engineered, recombinant, or chemically modified derivatives thereof, that specifically binds to a single type of target. For example, a monofunctional reagent may contain one or more functioning binding sites for an CD200 receptor. "Monofunctional reagent" also refers to a polypeptide, antibody, or other reagent that contains one or more functioning binding sites for, e.g., CD200 receptor and one or more non-functioning binding sites for Fe receptor. For example, a monofunctional reagent may comprise an antibody binding site for CD200 receptor plus an Fe fragment that has been engineered so that the Fe fragment does not specifically bind to Fc receptor.

"Bifunctional reagent" refers, e.g., to an antibody, binding composition derived from the binding site of an antibody, an antibody mimetic, a soluble receptor, engineered, recombinant, or chemically modified derivatives thereof, that specifically binds to two different targets, e.g., to an inhibiting CD200 receptor and an activating receptor. Generally, the bifunctional reagent will comprise binding sites from, e.g., two different antibodies, two different soluble receptors, or an antibody and a soluble receptor.

"Nucleic acid" refers to deoxyribonucleotides or ribonucleotides and polymers thereof in either single stranded or double-stranded form. The term nucleic acid may be used interchangeably with gene, cDNA, mRNA, oligonucleotide, and polynucleotide. A particular nucleic acid sequence also implicitly encompasses "allelic variants" and "splice variants."

"Specific binding" of a binding composition means that the binding composition binds to a specific antigen, e.g., CD200Ra (SEQ ID NO:2), with a binding constant ordinarily about 2-fold greater than to another antigen, typically about 4-fold greater than to another antigen, more typically at least about 10-fold greater than to another antigen, frequently at least about 40-fold greater than to another antigen; and most frequently at least about 100-fold greater than to another antigen.

"Ligand" refers to small molecules, peptides, polypeptides, and membrane associated or membrane-bound molecules that act as agonists or antagonists of a receptor, as well as to soluble versions of the above membrane-associated or membrane-bound molecules. Where the ligand is membrane-bound on a first cell, the receptor usually occurs on a second cell. The second cell may have the same or a different identity as the first cell. A ligand or receptor may be entirely intracellular, that is, it may reside in the cytosol, nucleus, or some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

"Humanized antibody" means an antibody comprising an antigen-binding region of nonhuman origin, e.g., rodent, and at least a portion of an immunoglobin of human origin, e.g., a human framework region, a human constant region, or portion thereof. See, e.g., U.S. Pat. No. 6,352,832.

"Immune condition" means, e.g., pathological inflammation, an inflammatory disorder, an inflammatory disease or disorder, or an autoimmune disorder or disease. "Immune condition" also refers to infections and cancerous conditions, e.g., pathological states where the immune system attempts to reduce the infection or reduce the cancerous condition. "Cancerous condition" includes, e.g., cancer, cancer cells, tumors, angiogenesis, and precancerous conditions such as dysplasia.

"Sample" refers to a sample from a human, animal, or to a research sample, e.g., a cell, tissue, organ, fluid, gas, aerosol, slurry, colloid, or coagulated material. The "sample" may be tested in vivo, e.g., without removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

"Therapeutically effective amount" of a therapeutic agent is defined as an amount of each active component of the pharmaceutical formulation that is sufficient to show a meaningful patient benefit, i.e., to cause a decrease in or amelioration of the symptoms of the condition being treated. When the pharmaceutical formulation comprises a diagnostic agent, "a therapeutically effective amount" is defined as an amount that is sufficient to produce a signal image, or other diagnostic parameter. Effective amounts of the pharmaceutical formulation will vary according to factors such as the degree of susceptibility of the individual, the age, gender, and weight of the individual, and idiosyncratic responses of the individual. See, e.g., U.S. Pat. No. 5,888,530.

II. GENERAL

The invention provides methods for the treatment and diagnosis of immune conditions, inflammatory conditions, and autoimmune disorders involving cells bearing CD200R, e.g., mast cells, antigen presenting cells (APCs), dendritic cells, neutrophils, T cells, monocytes, and macrophages. Dendritic cells are professional APCs. These conditions include, e.g., rheumatoid arthritis, bronchial hyperreactivity, asthma, allergic conditions, psoriasis, inflammatory bowel disease, multiple sclerosis, and pathological innate response, e.g., endotoxemia, sepsis, and septic shock. The invention contemplates methods of modulating a CD200R using, e.g., an agonist or an antagonist of CD200Ra or CD200Rb.

The invention contemplates use of binding compositions to CD200Ra, e.g., for inhibiting mast cells in the treatment of mast cell-dependent pathological conditions. Mast cells are implicated in the initiation and prolongation of rheumatoid arthritis (RA) (Lee, et al. (2002) Science 297:1689-1692; Vastag (2002) J. Am. Med. Assoc. 288:1457-1458; Woolley and Tetlow (2000) Arthritis Res. 2:65-74; Olsson, et al. (2001) Ann. Rheum. Dis. 60:187-193). Collagen-induced arthritis (CIA) is an experimental animal model for RA. RA and CIA involve, e.g., fibrin deposition, hyperplasia of synovial cells, periosteal bone formation, mononuclear infiltrates, pannus formation, and ankylosis of the joints (Luross and Williams (2001) Immunology 103:407-416). Immune cells, such as T cells and B cells, infiltrate the joints and induce pathology, e.g., inflammation, edema, or destruction of bone and cartilage. RA is, in part, an autoimmune disorder, wherein autoimmunity occurs against various proteins, including cartilage structural proteins (Griffiths and Remmers (2001) Immunol. Revs. 184: 172-183). CIA encompasses many features common to several human autoimmune diseases, e.g., RA, diabetes, multiple sclerosis, and autoimmune thyroiditis (Griffiths and Remmers, supra).

Mast cells also contribute to endotoxemia, which can be induced by administration of LPS to mice and related conditions (Tuncel, et al. (2000) Peptides 21:81-89; Duhamel, et al. (1997) J. Immunol. 158:2898-2903; Howard, et al. (1993) J. Exp. Med. 177:1205-1208). Endotoxemia correlates with sepsis, septic shock, infection with Gram negative and other bacteria, and adverse reactions in innate immunity (Cohen (2000) Intensive Care Med., 26 Suppl. 1: S51-56; Freise, et al. (2001) J. Invest. Surg. 14:195-212).

Mast cells and APCs have been implicated in the pathology of skin disorders, e.g., psoriasis and atopic dermatitis. Psoriasis occurs in over 4% of the population of Western countries. Psoriasis, which may be life threatening in some instances, is characterized by frequent relapses. It has also been associated with a form of arthritis known as psoriatic arthritis (Ackerman and Harvima (1998) Arch. Dermatol. Res. 290:353-359; Yamamoto, et al. (2000) J. Dermatol. Sci. 24:171-176; Ackerman, et al. (1999) Br. J. Dermatol. 140: 624-633; Schopf (2002) Curr. Opin. Invest. Drugs 3:720-724; Granstein (1996) J. Clin. Invest. 98:1695-1696; Christophers (2001) Clin. Exp. Dermatol. 26:314-320; Greaves and Weinstein (1995) New Engl. J. Med. 332:581-588; Robert and Kupper (1999) New Engl. J. Med. 341:1817-1828; Fearon and Veale (2001 Clin. Exp. Dermatol. 26:333-337; Mrowietz, et al. (2001) Exp. Dermatol. 10:238-245; Ackermann et al. (1999) Br. J. Dermatol. 140:624-633).

Asthma is another disorder involving mast cells, APCs, and other immune cells (Black (2002) New Engl. J. Med. 346: 1742-1743; Brightling, et al. (2002) New Engl. J. Med. 346: 1699-1705; Carroll, et al. (2002) Eur. Respir. J. 19:1-7; Xiang and Nilsson (2000) Clin. Exp. Allergy 30:1379-1386; Woodruff and Fahy (2001) J. Am. Med. Assoc. 286:395-398). Asthma is a chronic disorder characterized by bronchial hyperreactivity, which is the manifestation of pulmonary inflammatory disorders, including asthma, chronic obstructive pulmonary disease (a.k.a. COPD; chronic obstructive pulmonary disorder), chronic bronchitis, eosinophilic bronchitis, bronchiolitis, and viral bronchiolitis (Riffo-Vasquez and Spina (2002) *Pharmacol. Therapeutics* 94:185-211). Asthma is the result of a cascade of immune events, including the release of IgE. (See, e.g., Marone (1998) *Immunol. Today* 19:5-9; Barnes and Lemanske (2001) *New Engl. J. Med.* 344:350-362).

Mast cells contribute to the pathology of inflammatory bowel disease, e.g., Crohn's disease and colitis (Raithel, et al. (2001) *Scand. J. Gastroenterol.* 36:174-179; Nishida, et al. (2002) *Hepatogastroenterol.* 49:678-682; Gelbmann, et al. (1999) *Gut* 45:210-217; Nolte, et al. (1990) *Gut* 31:791-794; Jeziorska, et al. (2001) *J. Pathol.* 194:484-492). IgE activates mast cells resulting in constriction of the airways and damage by eosinophils to the airways.

Mast cells also contribute to the pathology of inflammatory conditions of the nervous system, e.g., multiple sclerosis (Robbie-Ryant, et al. (2003) *J. Immunol.* 170:1630-1634; Dines and Powell (1997) *J. Neuropathol. Exp. Neurol.* 56:627-640). These cells also play a role in allograft rejection, e.g., of the liver, kidney, and lung and graft versus host disease (GVHD), and glomerulonephritis (O'Keefe, et al. (2002) *Liver Transpl.* 8:50-57; Lajoie, et al. (1996) *Mod. Pathol.* 9:1118-1125; Yousem (1997) *Hum. Pathol.* 28:179-182; Levi-Schaffer and Weg (1997) *Clin. Exp. Allergy,* 27 Suppl. 1:64-70; Hiromura, et al. (1998) *Am. J. Kidney Dis.* 32:593-599). Mast cells have also been implicated in cardiovascular disease (Hara, et al. (2002) *J. Exp. Med.* 195:375-381).

In addition to mast cells, APCs have also been implicated in the mechanisms of disorders, such as, rheumatoid arthritis, allergies, asthma, endotoxemia, septic shock, and skin conditions, e.g., psoriasis (Santiago-Schwarz, et al. (2001) *J. Immunol.* 167:1758-1768; Lambrecht and Hammad (2003) *Curr. Opin. Pulm. Med.* 9:34-41; Eigenmann (2002) *Pediatr. Allergy Immunol.* 13:162-167; Curry, et al. (2003) *Arch. Pathol. Lab. Med.* 127:178-186; Supajatura, et al. (2002) *J. Clin. Invest.* 109:1351-1359; Koga, et al. (2002) *Dermatol.* 204:100-103).

The invention also contemplates a method of modulating a CD200R using, e.g., an antagonist of CD200Ra or an agonist of CD200Rb, in the treatment of infections or proliferative conditions, such as cancer and tumors. Mast cells, APCs, and other cells of the immune system play a role in preventing or combating infections, e.g., bacterial, viral, and protozoal infections. See, e.g., Marshall, et al. (2003) *Curr. Pharm. Dis.* 9:11-24; Malaviya and Georges (2002) *Clin. Rev. Allergy Immunol.* 22:189-204; Mekori and Metcalfe (2000) *Immunol. Rev.* 173:131-140; Galli, et al. (1999) *Curr. Opinion Immunol.* 11:53-59; Miles and Mamlok (1992) *J. Allergy Clin. Immunol.* 89:638-639; Sacks and Sher (2002) *Nature Immunol.* 3:1041-1047; Eigenmann (2002) *Pediatr. Allergy Immunol.* 13:162-171). Mast cells, APCs, or other cells of the immune system have also been found to participate in preventing or combatting proliferative conditions, e.g., cancer and tumors. See, e.g., Reay (2001) *Expert Opin. Ther. Targets* 5:491-506; Heckelsmiller, et al. (2002) *Eur. J. Immunol.* 32:3235-3245; Stift, et al. (2003) *Int. J. Oncol.* 22:651-656; Vermorken and Van Tendeloo (2003) *Expert Rev. Anticancer Ther.* 3:1-3.

III. CD200 RECEPTORS

Murine CD200Ra (a.k.a. muCD200Ra; SEQ ID NO:6) has a relatively long cytoplasmic tail. From in vivo studies, muCD200Ra is believed to be an inhibitory receptor, although it lacks a classical ITIM sequence. MuCD200Rb (SEQ ID NO:8), muCD200Rc (SEQ ID NO:10) and muCD200Rd (SEQ ID NO:12) have short cytoplasmic tails, charged amino acids in their transmembrane regions, and have been shown to pair with a cellular activating adaptor molecule, Dap12 (Lanier and Bakker (2000) *Immunol. Today* 21:611-614). Human CD200Ra is homologous to murine CD200Ra. Human CD200Rb (SEQ ID NO:4) is most homologous to muCD200Rb/d and is also a pairing partner with Dap12.

IV. PURIFICATION AND MODIFICATION OF POLYPEPTIDES

Polypeptides, e.g., antigens, antibodies, and antibody fragments, for use in the contemplated method can be purified by methods that are established in the art. Purification may involve homogenization of cells or tissues, immunoprecipitation, and chromatography. Stability during purification or storage can be enhanced, e.g., by anti-protease agents, antioxidants, ionic and non-ionic detergents, and solvents, such as glycerol or dimethylsulfoxide.

Modification to proteins and peptides include epitope tags, fluorescent or radioactive groups, monosaccharides or oligosaccharides, sulfate or phosphate groups, C-terminal amides, acetylated and esterified N-groups, acylation, e.g., fatty acid, intrachain cleaved peptide bonds, and deamidation products (Johnson, et al. (1989) *J. Biol. Chem.* 264:14262-14271; Young, el. (2001) *J. Biol. Chem.* 276:37161-37165). Glycosylation depends upon the nature of the recombinant host organism employed or physiological state (Jefferis (2001) *BioPharm* 14:19-27; Mimura, et al. (2001) *J. Biol. Chem.* 276:45539-45547; Axford (1999) *Biochim. Biophys. Acta* 1:219-229; Malhotra, et al. (1995) *Nature Medicine* 1:237-243).

Derivatives of polypeptides also include modification by a fusion protein partner (Ausubel, et al. (2001) *Current Protocols in Molecular Biology* Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391).

V. BINDING COMPOSITIONS

Antibodies can be derived from human or non-human sources. Intact protein, denatured protein, or a peptide fragment of the protein, may be used for immunization (Harlow and Lane, supra, pp. 139-243). Regions of increased antigenicity may be used for peptide fragment immunization. Human CD200Ra (SEQ ID NO:2) has regions of increased antigenicity, e.g., at amino acids 43-47, 62-66, 109-114, 165-174, 187-199, 210-214, 239-244, 260-267, and 293-300 of SEQ ID NO:2 (Vector NTI® Suite, InforMax, Inc., Bethesda, Md.). Human CD200Rb (SEQ ID NO:4) is unusually antigenic at amino acids 55-75 of SEQ ID NO:4. Mouse CD200Ra (SEQ ID NO:6) has regions of increased antigenicity at amino acids 25-40 and amino acids 85-95 of SEQ ID NO:6. Mouse CD200Rb (SEQ ID NO:8) has regions of increased antigenicity at amino acids 10-22, 85-90, and 105-120 SEQ ID NO:8. Mouse CD200Rc (SEQ ID NO:10) has regions of increased antigenicity at amino acids 20-40, 115-130, and 190-220 of SEQ ID NO:10. Mouse CD200Rd has regions of increased antigenicity at amino acids 20-50, 90-120, 155-175, and 180-200 of SEQ ID NO:12 (MacVector 6.5®, Accelrys, San Diego, Calif.). This list of antigenic fragments and regions is not intended to limit the regions of the polypeptides that can be used to raise antibodies or that can be bound by antibodies.

Binding compositions comprising an extracellular domain of CD200, or antigenic fragments thereof, are contemplated, e.g., in mono- and bifunctional agents. The extracellular domain of human, mouse, and rat CD200 is described (Chen, et al. (1997) *Biochim. Biophys. Acta* 1362:6-10).

Antibodies derived from murine or other non-human sources can provoke an immune response, provide weak recruitment of effector function, or show rapid clearance from the bloodstream (Baca, et al. (1997) *J. Biol. Chem.* 272: 10678-10684). For these reasons, it may be desired to prepare therapeutic antibodies by humanization. A humanized antibody contains the amino acid sequences from six complementarity determining regions (CDRs) of the parent mouse antibody, that are grafted on a human antibody framework. The content of non-human sequence in humanized antibodies is preferably low, i.e., about 5% (Baca, et al. (1997) *J. Biol. Chem.* 272:10678-10684). To achieve optimal binding, the humanized antibody may need fine-tuning, by changing certain framework amino acids, usually involved in supporting the conformation of the CDRs, back to the corresponding amino acid found in the parent mouse antibody. The framework amino acids that are generally changed back to those of the parent are those involved in supporting the conformation of the CDR loops (Chothia, et al. (1989) *Nature* 342:877-883; Foote and Winter (1992) *J. Mol. Biol.* 224:487-499). The framework residues that most often influence antigen binding is relatively small, and may be a small as eleven residues (Baca, et al. (1997) *J. Biol. Chem.* 272:10678-10684).

Humanized antibodies include antibodies having all types of constant regions, including IgM, IgG, IgD, IgA and IgE, and any isotype, including IgG1, IgG2, IgG3 and IgG4. When it is desired that the humanized antibody exhibit cytotoxic activity, the constant domain is usually a complement-fixing constant domain and the class is typically IgG1. When such cytotoxic activity is not desirable, the constant domain can be of the IgG2 class. The humanized antibody may comprise sequences from more than one class or isotype (U.S. Pat. No. 6,329,511 issued to Vasquez, et al.).

An alternative to humanization is to use human antibody libraries displayed on phage or human antibody libraries in transgenic mice (Vaughan, et al. (1996) *Nature Biotechnol.* 14:309-314; Barbas (1995) *Nature Medicine* 1:8317-839; Mendez. et al. (1997) *Nature Genetics* 15:146-156; Hoogenboom and Chames (2000) *Immunol. Today* 21:371-377; Barbas, et al. (2001) *Phage Display: A Laboratory Manual*, Cold Spring Harbor Laboratory Press, Cold Spring Harbor, N.Y.; Kay, et al. (1996) *Phage Display of Peptides and Proteins: A Laboratory Manual*, Academic Press, San Diego, Calif.; de Bruin, et al. (1999) *Nature Biotechnol.* 17:397-399).

Bifunctional antibodies are provided. See, e.g., Mack, et al. (1995) *Proc. Natl. Acad. Sci. USA* 92:7021-7025; Carter (2001) *J. Immunol. Methods* 248:7-15; Volkel, et al. (2001) *Protein Engineering* 14:815-823; Segal, et al. (2001) *J. Immunol. Methods* 248:1-6; Brennan, et al (1985) *Science* 229:81; Raso, et al. (1997) *J. Biol. Chem.* 272:27623; Morrison (1985) *Science* 229:1202; Traunecker, et al. (1991) *EMBO J.* 10:3655; and U.S. Pat. Nos. 5,932,448, 5,532,210, and 6,129,914. Single chain antibodies and diabodies are described. See, e.g., Malecki, et al. (2002) *Proc. Natl. Acad. Sci. USA* 99:213-218; Conrath, et al. (2001) *J. Biol. Chem.* 276:7346-7350; Desmyter, et al. (2001) *J. Biol. Chem.* 276: 26285-26290; Hudson and Kortt (1999) *J. Immunol. Methods* 231:177-189; and U.S. Pat. No. 4,946,778.

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (Meyaard, et al. (1997) *Immunity* 7:283-290; Wright, et al. (2000) *Immunity* 13:233-242; Preston, et al., supra; Kaithamana, et al. (1999) *J. Immunol.* 163:5157-5164).

Therapeutic antibodies may be conjugated, e.g., to small drug molecules, enzymes, liposomes, polyethylene glycol (PEG), or fusion protein antibodies. See, e.g., van Oosterhout, et al. (2001) *Int. J. Pharm.* 221:175-186; Marsh and Klinman (1990) 144:1046-1051; Kreitman (2001) *Curr. Pharm. Biotechnol.* 2:313-325; Dinndorf, et al. (2001) *J. Immunother.* 24:511-516; Wahl et al. (2001) *Int. J. Cancer* 93:540-600; Garber (2000) *J. Nat. Cancer Instit.* 92:1462-1464; Everts, et al. (2002) *J. Immunol.* 168:883-889; Chen, et al. (2001) *Int. J. Cancer* 94:850-858; Shaik, et al. (2001) *J. Control. Release* 76:285-295; Park, et al. (2001) *J. Control. Release* 74:95-113; Solorzano, et al. (1998) *J. Appl. Physiol.* 84:1119-1130; Rosenberg, et al. (2001) *J. Appl. Physiol.* 91:2213-2223; Bendele, et al. (2000) *Arthritis Rheum.* 43:2648-2659; Trakas and Tzartos (2001) *J. Neurochem.* 120: 42-49; Chapman, et al. (1999) *Nature Biotechnol.* 17:780-783; Gaidamakova, et al. (2001) *J. Control. Release* 74:341-347; Coiffier, et al. (2002) *New Engl. J. Med.* 346:235-242.

Antibodies are useful for diagnostic or kit purposes, and include antibodies coupled, e.g. to dyes, radioisotopes, enzymes, or metals, e.g., colloidal gold (Le Doussal, et al. (1991) *J. Immunol.* 146:169-175; Gibellini, et al. (1998) *J. Immunol.* 160:3891-3898; Hsing and Bishop (1999) *J. Immunol.* 162:2804-2811; Events, et al. (2002) *J. Immunol.* 168: 883-889).

VI. INHIBITING AND ACTIVATING RECEPTORS

The invention provides methods for cross-linking two different receptors, e.g., an inhibiting receptor and an activating receptor, for modulating cell activity.

Examples of inhibiting receptors include, e.g., FcγRIIB, LAIR, FDF03, KIR, gp49B, ILT25, PIR-B, Ly49, CTLA-4, CD200Ra (SEQ ID NO:2), CD94/NKG2A, NKG2B-E, PECAM-1, CD5, CD22, CD72, PIR1, SIRPα, HM18, LRC, ILT, KIR, LIR, MIR, and MAFA. See e.g., Long (1999) *Ann. Rev. Immunol.* 17:875-904; Lanier (1997) *Immunity* 6:371-378; Sinclair (1999) *Scan. J. Immunol.* 50:10-13; Pan, et al. (1999) *Immunity* 11:495-506) Inhibiting receptors also include DNAX Surface Protein-1 (a.k.a. DSP-1) (Cantoni, et al. (1999) *Eur. J. Immunol.* 29:3148-3159.

Activating receptors include, e.g., CD3, CD2, CD10, CD161, Dap12, KAR, KARAP, FcεRI, FCεRII, FcγRIIA, FcγRIIC, FcγRIII/CD16, Trem-1, Trem-2, CD28, p 44, p 46, B cell receptor, LMP2A, STAM, STAM-2, GPVI, and CD40. See, e.g., Azzoni, et al. (1998) *J. Inmmunol.* 161:3493-3500; Kita, et al. (1999) *J. Immunol.* 162:6901-6911; Merchant, et al. (2000) *J. Virol.* 74:9115-9124; Pandey, et al. (2000) *J. Biol. Chem.* 275:38633-38639; Zheng, et al. (2001) *J. Biol Chem.* 276:12999-13006; Propst, et al. (2000) *J. Immunol.* 165: 2214-2221.

The invention provides methods for inhibiting, e.g., lymphoid cells, myeloid cells, and endothelial cells. Cell inhibition is accomplished, e.g., by treating a cell, tissue, organ, extracellular fluid, animal, human subject, or cells or tissues ex vivo, with a mono-, bi-, or multifunctional reagent or binding composition.

Agents that modulate expression of receptors, e.g., on a cell surface, are described. See, e.g., van de Winkel, et al. (1991) *J. Leukocyte Biol.* 49:511-524; van de Winkel, et al. (1993) *Immunol. Today* 14:215-221; Heijnen, et al. (1997) *Intern. Rev. Immunol.* 16:29-55; Fridman and Sautes (1996) *Cell-Mediated Effects of Immunoglobins*, Chapman and Hall, New York, N.Y., pp. 39-40). The invention encompasses using an agent to increase expression of an inhibiting receptor, such as CD200Ra (SEQ ID NO:2), in order to increase efficiency of interaction of a binding composition specific for CD200Ra with CD200Ra, e.g., associated with mast cells, APCs, neutrophils, T cells, B cells, hasophils, eosinophils, or epithelial cells. Also contemplated is use of an agent to increase expression of an activating receptor, such as CD200Rb (SEQ ID NO:4). The agent may comprise, e.g., a cytokine such as interferon or IL-10, a growth factor, a bifunctional reagent, an enzyme, or a small molecule such as adenosine. The agent may comprise a factor that promotes maturation of, e.g., mast cells, dendritic cells, or other APCs, or neutrophils, such as, stem cell factor, granulocyte-macrophage colony-stimulating factor, tumor necrosis factor, or IL-6 (Hjertson, et al. (1999) *Brit. J. Haematol.* 104:516-522; Austen and Boyce (2001) *Leuk. Res.* 25:511-518; Vandenabeele and Wu (1999) *Immunol. Cell Biol.* 77:411-419; Santiago-Schwarz (1999) *J. Leuk. Biol.* 66:209-216; Liu, et al. (2001) *Nat. Immunol.* 2:585-589; Kondo, et al. (2003 *Ann. Rev. Immunol.*; Dumortier, et al. (2003) *Blood* 101:2219-2226).

VII. SCREENING

Assays comprising animals, cells, or reagents such as beads or wells, are contemplated for screening for CD200, CD200R, and for agents that modulate interactions between CD200 and CD200R. See, e.g., Steinitz (2000) *Analyt. Biochem.* 232:238; Gast, et al. (1999) *Analyt. Biochem.* 276:227-241; Kaiser, et al. (2000) *Analyt. Biochem.* 282:173-185; and U.S. Pat. Nos. 6,176,962 and 6,517,234.

Cells or animals can be engineered, e.g., to express a CD200R, in order to facilitate their use in screening. Expression can be measured by, e.g., by hybridization-based techniques (Ausubel, et al. (2001) *Curr. Protocols Mol. Biol.*, Vol. 4, John Wiley and Sons, New York, N.Y., pp. 25.0.1-25B.2.20; Ausubel, et al. (2001) *Curr. Protocols Mol. Biol.*, Vol. 3, John Wiley and Sons, New York, N.Y., pp. 14.0.1-14.14.8; Liu, et al. (2002) *Analyt. Biochem.* 300:40-45; Huang, et al. (2000) *Cancer Res.* 60:6868-6874; Wittwer, et al. (1997) *Biotechniques* 22:130-138; Schmittgen, et al. (2000) *Analyt. Biochem.* 285:194-204; Heid, et al. (1996) *Genome Res.* 6:989-994). Polypeptides can be detected, e.g., by antibody-based techniques. See, e.g., Harlow and Lane, supra, pp. 553-612; Sims, et al. (2000) *Analyt. Biochem.* 281:230-232.

VIII. THERAPEUTIC COMPOSITIONS

Formulations of, e.g., binding compositions, binding compounds, or antibodies, are prepared by mixing, e.g., the antibody having the desired degree of purity with optional physiologically acceptable carriers, excipients, or stabilizers in the form of lyophilized cake or aqueous solutions. See, e.g., Hardman, et al. (2001) *Goodman and Gilman's the Pharmacological Basis of Therapeutics*, McGraw-Hill, New York, N.Y.; and Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; and Lieberman, et at. (eds.) (1990) *Pharmaceutical Dosage Forms: Disperse Systems* Dekker, NY. The therapeutic or pharmaceutical of this invention may be combined with or used in association with, e.g., anti-inflammatory, chemotherapeutic or chemopreventive agents. Acceptable carriers, excipients, buffers, stabilizers, and surfactants are described. See, e.g., U.S. Pat. Nos. 6,342,220; 5,440,021; 6,096,728; and Weiner and Kotkoskie (2000) *Excipient Toxicity and Safety*, Marcel Deekker, Inc., New York, N.Y.

Therapeutic antibody compositions generally are placed into a container having a sterile access port, for example, an intravenous solution bag or vial having a stopper pierceable by a hypodermic injection needle. The route of antibody administration is, e.g. injection or infusion by intravenous, intraperitoneal, intracerebral, intramuscular, intraocular, intraarterial, intracerebrospinal, intralesional, or pulmonary routes, or by sustained release systems. Sustained release systems are described. See, e.g.; Sidman et al. (1983) *Biopolymers,* 22:547-556; Langer et al. (1981) *J. Biomed. Mater. Res.* 15:167-277; Langer (1982) *Chem. Tech.* 12:98-105; Epstein et al. (1985) *Proc. Natl. Acad. Sci. USA* 82:3688-3692; Hwang et al. (1980) *Proc. Natl. Acad. Sci. USA* 77:4030-4034; U.S. Pat. Nos. 6,350,466 and 6,316,024.

An "effective amount" of antibody to be employed therapeutically will depend, e.g., upon the therapeutic objectives, the route of administration, e type of antibody employed, and the condition of the patient. Accordingly, it will be necessary for the therapist to titer the dosage and modify the route of administration as required to obtain the optimal therapeutic effect. Typically, the clinician will administer the antibody until a dosage is reached that achieves the desired effect. The progress of this therapy is easily monitored by conventional assays.

In the treatment or prevention of, e.g., an inflammatory or proliferative disorder, by the contemplated method, the binding composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners. The "therapeutically effective amount" of antibody to be administered will be governed by such considerations, and is the minimum amount necessary to prevent, ameliorate, or treat the proliferative disorder. Such amount is preferably below the amount that is toxic to the host.

As a general proposition, the initial pharmaceutically effective amount of the antibody administered parenterally will be in the range of about 0.1 µg/kg to 10 mg/kg of the patient's body weight per day, ordinarily 0.1 µg/kg/day to 1.0 mg/kg/day, preferably 0.1 µg/kg/day to 0.1 mg/kg/day, more preferably 0.1 µg/kg/day to 0.01 mg/kg/day, and most preferably 0.1 µg/kg/day, or less. The desired dosage can be delivered by a single bolus administration, by multiple bolus administrations, or by continuous infusion administration of antibody, depending on the pattern of pharmacokinetics that the practitioner wishes to achieve. As noted above, however, these suggested amounts of antibody are subject to a fair amount of therapeutic discretion, The key factor in selecting an appropriate dose and scheduling is the result obtained.

IX. SECONDARY THERAPEUTICS

The invention contemplates use of combinations of an agonist or antagonist of CD200R with a second agent, e.g., an anti-inflammatory, immunosuppressive, or anti-neoplastic agent. Anti-inflammatory agents include, e.g., steroids and non-steroidal anti-inflammatories (U.S. Pat. No. 6,294,170 issued to Boone, et al.; U.S. Pat. No. 6,096,728 issued to Collins, et al.; Hardman, et al. (2001) *Goodman and Gilman's the Pharmacological Basis of Therapeutics*, McGraw-Hill, New York, N.Y.). Immunosuppressive agents include, e.g., azothioprine, mercaptopurine, and methotrexate. Anti-neoplastic agents include, e.g., 5-fuorouracil, methotrexate, cisplatin, and doxorubicin (U.S. Pat. No. 6,066,668 issued Hausheer, et al.).

X. KITS

The contemplated method is adapted for use in kits, i.e., for screening or diagnostic purposes. The kit may be adapted for use in detecting or quantitating a binding composition to CD200R, e.g., in a pharmaceutical composition or in a biological sample. The contemplated kit is adapted for use with, e.g., mast cells from a subject or patient. Typically, the kit will have a compartment, a reagent, or directions for use or disposal, or any combination thereof. Kits adapted to binding assays are described, e.g., U.S. Pat. Nos. 6,306,608; 6,150,122; 6,083,760; and 5,863,739.

XI. USES

The present invention contemplates methods for using a binding composition specific for a CD200R to modulate disorders associated with improper function of cells of the immune system, e.g., mast cells, APCs, such as dendritic cells, T cells neutrophils, monocytes, or macrophages. The binding composition may comprise an agonist or antagonist of a CD200R. Agonists of an inhibiting receptor, e.g., CD200Ra (SEQ ID NOs:2 or 6), will be useful in inhibiting activity of mast cells, APCs, such as dendritic cells, T cells, neutrophils, monocytes, or macrophages. Antagonists of an activating receptor, e.g., CD200Rb (SEQ ID NOs:4, 6, 10, or 12) will also be useful in inhibiting activity of, e.g., mast cells, APCs, such as dendritic cells, T cells, neutrophils, monocytes, or macrophages. Antagonists of CD200Ra and agonists of CD200Rb will be useful for stimulating, e.g., mast cells and APCs, such as dendritic cells, T cells, neutrophils, monocytes, or macrophages, for the treatment of infections and proliferative conditions.

The methods of the present invention contemplate use of, e.g., peptides, small molecules, antibodies, and binding compositions derived from the antigen binding site of an antibody, to treat or diagnose a variety of immune disorders, e.g., bronchial hyperreactivity, allergic rhinitis, asthma, bronchitis, and anaphylaxis. See, e.g., Woodruff and Fahy, supra; Plaut (2001) *J. Am. Med. Assoc.* 286:3005-3006; and Marshall and Bienenstock (1994) *Curr. Op. Immunol.* 6:853-859; Luskin and Luskin (1996) *Am. J. Ther.* 3:515-520.

The methods of the present invention can also be used to treat or diagnose rheumatoid arthritis, and skin disorders including psoriasis and atopic dermatitis. See, e.g., Mican and Metcalfe (1990) *J. Allergy Clin. Immunol.* 86:677-683; Malone, et al. (1987) *Arthritis Rheum.* 30:130-137; Malfait, et al. (1999) *J. Immunol.* 162:6278-6280; Ackermann and Harvima (1998) *Arch. Dermatol. Res.* 290:353-359; Ackermann, et al. (1999) *Brit. J. Dermatol.* 140:624-633; Askenase, et al. (1983) *J. Immunol.* 131:2687-2694. The method also contemplates treatment or diagnosis of inflammatory diseases of the gastrointestinal tract, e.g., Crohn's disease, ulcerative colitis, and irritable bowel syndrome. See, e.g., Malaviya, et al. (1995) *Am. J. Ther.* 2:787-792; Jeziorska, et al. (2001) *J. Pathol.* 194:484-492; Sullivan, et al (2000) *Neurogastroenterol. Motility* 12:449; Nolte, et al. (1990) *Gut* 31:791-794; Raithel, et al. (2001) *Scand. J. Gastroenterol.* 36:174-179. The method is also contemplated for use in treating chronic liver disease and congestive heart failure (O'Keefe, et al. (2002) *Liver Transpl.* 8:50-57; Hara, et al. (2002) *J. Exp. Med.* 195:375-381).

The invention also encompasses methods of treatment or diagnosis of demyclination or neurodegeneration, e.g., multiple sclerosis, Guillain-Barre syndrome, Alzheimer's disease, Parkinson's disease, and epilepsy (Purcell and Atterwill (1995) *Neurochem. Res.* 20:521-532: Secor, et al. (2000), *J. Exp. Med.* 191:813-822; Dines and Powell (1997) *J. Neuropathol. Exp. Neurol.* 56:627-640; Purcell and Atterwill (1995) *Neurochem. Res.* 20:521-532; Dietsch and Hinrichs (1989) *J. Immunol.* 142:1476-1481).

Moreover the invention encompasses a method of treating or diagnosing Sjogren's syndrome, transplant and graft rejection, graft-versus-host disease (GVHD), mastocytosis, and methods for preventing angiogenesis (Pedersen and Nauntofte (2001) *Expert Opin. Pharmacother.* 2:1415-1436; Konttinen, et al. (2000) *Rheumatol. Int.* 19:141-147; Moutsopoulos and Youinou (1991) *Curr. Opin. Rheumatol.* 3:815-822, Corczynski, et al. (2000) *Clin. Immunol.* 95:182-189; Koskinen, et al. (2001) *Transplantation* 71:174-1747; O'Keefe, et al. (2002) *Liver Transpl.* 8:50-57; Lajoie, et al. (1996) *Mod. Pathol.* 9:1118-1125; Pardo, et al. (2000) *Virchows Arch.* 437:167-172; Yousem (1997) *Hum. Pathol.* 28:179-182; and Levi-Sehaffer and Wej (1997) *Clin. Exp. Allergy* 27 Suppl. 1:64-70; Tomita, et al. (2000) *Ann. Thorac. Surg.* 69:1686-1690; Brockow and Metcalfe (2001) *Curr. Opin. Allergy Clin. Immunol.* 1:449-454; Hiromatsu and Toda (2003) *Microsc. Res. Tech.* 60:64-69).

Yet another aspect of the invention provides methods of modulating activity of a CD200R, e.g., SEQ ID NO:2, for the treatment or prevention of cardiovascular disease, e.g., atherosclerosis. Immune cells, e.g., mast cells, dendritic cells, neutrophils, monocytes, and macrophages, contribute to the pathology of atherosclerosis. See, e.g., Huang, et al. (2002) *Cardiovasc. Res.* 55:150-160; Kelley, et al. (2000) *Mol. Med. Today* 6:304-308; Aicher, et al. (2003) *Circulation* 107:604-611; Ozmen, et al. (2002) *Histol. Histopathol.* 17:223-237; Wanders, et al. (1994) *Transpl. Int.* 7 Suppl. 1:S371-S375.

Also encompassed are methods of providing an antagonist of CD200Ra (SEQ ID NO:2) or an agonist of CD200Rb (SEQ ID NO:4) to stimulate cell activity, e.g., to combat bacterial infections, viral infections, persistent infections, infections by foreign multi-cellular organisms, cancerous conditions and tumors, and to promote wound healing.

The broad scope of this invention is best understood with reference to the following examples, which are not intended to limit the inventions to the specific embodiments.

EXAMPLES

I. General Methods

Methods for the diagnosis and treatment of inflammatory conditions in animals and in humans are described. See, e.g., Ackerman (1997) *Histological Diagnosis of Inflammatory Skin Disease*, $2^{nd}$ ed., Lippincott, Williams, and Wilkins, New York, N.Y.; Gallin, et al. (1999) *Inflammation: Basic Principles and Clinical Correlates*, $3^{rd}$ ed., Lippincott, Williams, and Wilkins, New York, N.Y.; Geppetti and Holzer (1996) *Neurogenic Inflammation*, CRC Press, Boca Raton, Fla.; Nelson, et al. (2000) *Cytokines in Pulmonary Disease: Infection and Inflammation*, Marcel Dekker, Inc., New York, N.Y.; O'Byrne (1990) *Asthma as an Inflammatory Disease*, Marcel Dekker, Inc., New York, N.Y., Parnham, et al. (1991) *Drugs in Inflammation (Agents and Actions Suppl., Vol. 32)*, Springer Verlag, Inc., New York, N.Y.; Benezra (1999) *Ocular Inflammation: Basic and Clinical Concepts*, Blackwell Science, Ltd., Oxford, UK.

Standard methods in molecular biology are described (Maniatis, et al. (1982) *Molecular Cloning, A Laboratory Manual*, Cold Spring Harbor Laboratory Press, Cold Spring Harbor, N.Y.; Sambrook and Russell (2001) *Molecular Cloning*, 3rd ed., Cold Spring Harbor Laboratory Press, Cold Spring Harbor, N.Y.; Wu (1993) *Recombinant DNA, Vol.* 217, Academic Press, San Diego, Calif.). Standard methods also appear in Ausbel, et al. (2001) *Current Protocols in Molecular Biology. Vols.* 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, and glycosylation of proteins are described (Coligan, et al. (2000) *Current Protocols in Protein Science Vol.* 2, John Wiley and Sons, Inc., New York). Production, purification, and fragmentation of polyclonal and monoclonal antibodies is described (Coligan, et al. (2001) *Current Protocols in Immunology Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane supra.

Standard techniques for characterizing ligand/receptor interactions are available. See, e.g., Coligan, et al. (2001) *Current Protocols in Immunology. Vol.* 4, John Wiley and Sons, Inc., New York.

Standard techniques in cell and tissue culture are described. See, e.g., Freshney (2000) *Culture of Animal Cells: A Manual of Basic Tech,* 4th ed., Wiley-Liss, Hoboken, N.J.; Masters (ed.) (2000) *Animal Cell Culture: A Practical Approach,* 3rd ed., Oxford Univ. Press, Oxford, UK; Doyle, et al. (eds.) (1994) *Cell and Tissue Culture: Laboratory Procedures*, John Wiley and Sons, NY; Melamed, et al. (1990) *Flow Cytometry and Sorting* Wiley-Liss, Inc., New York, N.Y.; Shapiro (1988) *Practical Flow Cytometry Liss*, New York, N.Y.; Robinson, et al. (1993) *Handbook of Flow Cytometry Methods* Wiley-Liss, New York, N.Y.

Animal models for arthritis, multiple sclerosis, psoriasis, and lipopolysaccharide (LPS)-induced inflammation are available. See, e.g., Luross and Williams (2001) *Immunology* 103:407-416; Griffiths and Remmers (2001) *Immunol. Rev.* 184:172-183; Beurler (2000) *Curr. Opin. Immunol.* 12:20-26; Campbell, et al. (1998) *J. Immunol.* 161:3639-3644; Tompkins, et al. (2002) *J. Immunol.* 168:4173-4183; Hong, et al. (1999) *J. Immunol.* 162:7480-7491.

Software packages for determining, e.g., antigenic fragments, signal and leader sequences, protein folding, and functional domains, are available. See, e.g., Vector NTI® Suite (Informax, Inc., Bethesda, Md.); GCG Wisconsin Package (Accelrys, Inc., San Diego, Calif.), and DeCypher® (TimeLogic Corp., Crystal Bay, Nev.); Menne, et al. (2000) *Bioinformatics* 16:741-742. Public sequence databases were also used, e.g., from GenBank and others.

II. Preparation of Mast Cells

Murine mast cell cultures were established from 2-3 week old C57BL/6 mice. Bone marrow was flushed from the femurs of 2-3 mice and subsequently washed three times with phosphate buffered saline (PBS). Cells were resuspended in 15 ml Dulbecco's minimal essential media (MEM) supplemented with sodium pyruvate, non-essential amino acids, 2-mercaptoethanol, N-2-hydroxyetliylpiperazine-N'-2-ethanesulfonic acid (HEPES), glutamine, 10-15% fetal calf serum (Hyclone, Inc., Logan, Utah), 100 ng/mg rSCF, and 100 ng/ml of rIL-3. Cells were incubated in T25 flasks at 37° C. At weekly intervals, the non-adherent cells were refed with fresh media and transfered to a new flask. At two weeks, culture media was supplemented with 5.0 ng/ml of IL-4. By four weeks, the majority of non-adherent cells are expected to be typical murine mast cells expressing IgE FcR. From four weeks on, the cells were maintained with supplements of only rIL-3 and rIL-4.

III. Distribution of CD200R

Total RNA was isolated from a variety of cell types and tissues using the RNEASY® RNA isolation kit (Qiagen, Inc., Valencia, Calif.). RNA was reverse transcribed using oligo dT primers and Multiscrib reverse transcriptase (Applied Biosystems, Inc., Foster City, Calif.). cDNA was analyzed for expression of CD200 receptors and ubiquitin by Taqman® PCR assays using a Perkin Elmer ABI Prism 5700® sequence detection system (Perkin Elmer, Inc., Wellesley, Mass.). Quantitation of target gene expression was calculated by normalizing the values relative to the expression of ubiquitin.

Results of Taqman® analysis are presented in Table 1. Highest expression is represented by (+++), moderate expression is (++) or (+) while borderline to undetectable on levels is (−). ND means not determined.

TABLE 1

| Cell or tissue | Human CD200Ra (SEQ ID NOs: 1, 2) | Human CD200Rb (SEQ ID NO: 3, 4) | Mouse CD200Ra (SEQ ID NO: 5, 6) | Mouse CD200Rb (SEQ ID NO: 7, 8) | Mouse CD200Rc (SEQ ID NO: 9, 10) | Mouse CD200Rd (SEQ ID NO: 11, 12) |
|---|---|---|---|---|---|---|
| Mast cells | (++) | (+++) | (++) | (+++) | (+++) | (+++) |
| Macrophages resting ex bone marrow | ND | ND | (+++) | (+++) | (−) | (++) |
| Macrophages activated LPS + IFNg + IL-10 24 hour ex bone marrow | ND | ND | (++) | (++) | (−) | (++) |
| Brain Macrophages (microglia) | ND | ND | (+) | (+) | (−) | (+) |
| Activated microglia | ND | ND | (+) | (++) | (−) | (++) |

TABLE 1-continued

| Cell or tissue | Human CD200Ra (SEQ ID NOs: 1, 2) | Human CD200Rb (SEQ ID NO: 3, 4) | Mouse CD200Ra (SEQ ID NO: 5, 6) | Mouse CD200Rb (SEQ ID NO: 7, 8) | Mouse CD200Rc (SEQ ID NO: 9, 10) | Mouse CD200Rd (SEQ ID NO: 11, 12) |
|---|---|---|---|---|---|---|
| Monocytes | (+) | (+, −) | ND | ND | ND | ND |
| Dendritic cells | (+++) | (+++) | (+) | (++) | (+) | (+) |
| B cells | (+, −) | (+) | (+, −) | (+, −) | (−) | (+, −) |
| T cell C57BL/6 TH1 activated pool | ND | ND | (+, −) | (+, −) | (−) | (−) |
| T cell C57BL/6 TH2 activated pool | ND | ND | (++) | (++) | (+, −) | (+) |
| T cell TH1 activated pool | (−) | (−) | ND | ND | ND | ND |
| T cell TH2 activated pool | (+) | (−) | ND | ND | ND | ND |
| NK cell | (−) | (−) | ND | ND | ND | ND |
| Endothelial cell | ND | ND | (−) | (+) | (−) | (−) |
| Fibroblast | (−) | (+, −) | (−) | (−) | (−) | (−) |
| Aorta atherosclerosis Model | ND | ND | (+++) | (+++) | (−) | (+++) |
| Colon | (++) | (−) | (+) | (++) | (+, −) | (+) |
| Lung | (++) | (++) | (+++) | (++) | (++) | (++) |
| Lung hypersensitivity pneumonitis | (+++) | ND | ND | ND | ND | ND |
| Fibroblast hypersensitivity pneumonitis | (+++) | ND | ND | ND | ND | ND |
| Eosinophilic granuloma | (++) | ND | ND | ND | ND | ND |
| Lung idiopathic pulmonary fibrosis | (++) | ND | ND | ND | ND | ND |
| Infiltrating cells rheumatoid arthritis | (+++) | ND | ND | ND | ND | ND |
| Skin | (−) | (−) | (++) | (+) | (+) | (+) |
| Spinal cord C57BL/6 TNFα knockout, untreated | ND | ND | (+, −) | (+, −) | (−) | (−) |
| Spinal cord C57BL/6 TNFα knockout EAE model | ND | ND | (+) | (+) | (−) | (++) |
| Spleen | ND | ND | (++) | (+) | (++) | (+) |

Iv. Association of CD200R with Dap12

To verify the association of CD200 receptors with Dap12, CD200 receptors were introduced by retrovirus vectors into Baf cell lines that had previously been transfected with one of the following FLAG-tagged molecules. Dap12, Dap10, FcεRγ, or CD3-ζ. The FLAG-tagged molecules are only expressed on the cell surface when stably associated with appropriate pairing partner molecule. When murine CD200Rc (SEQ ID NO:10) or murine CD200Rd (SEQ ID NO:12) was introduced into these transfectants, only FLAG-tagged Dap12 was rescued indicating that these CD200 receptors specifically pair with Dap12.

V. Agonist Antibodies of CD200R

Epitope-tagged CD200R molecules were stably introduced into normal mouse mast cells. These CD200Rs were then directly engaged with monoclonal antibodies specific for various epitope tags. Mast cell degranulation, cytokine secretion, and proliferation were monitored with and without subsequent cross-linking of the anti-tag antibodies. Triggering CD200Ra had no effects on resting mast cells, however, triggering the CD200 receptors that pair with Dap12, i.e., activating CD200Rs, caused significant mast cell degranulation, cytokine secretion, and autocrine-dependent proliferation.

Epitope-tagged CD200Ra was stably introduced into normal mast cells. CD200Ra (SEQ ID NO:6) farther comprising an epitope tag was engaged by a CD200 Ig-fusion protein or by monoclonal antibodies against the epitope tags while simultaneously activating the FcεRI with IgE antibodies. Mast cells were then monitored for degranulation, cytokine secretion, and proliferative responses. In some experiments, CD200Ra and FcεRI were co-ligated by a secondary antibody. The results demonstrated that CD200Ra is an inhibitory receptor capable of inhibiting FcεRI-dependent responses in mast cells.

In related studies, monoclonal antibodies specific for murine CD200Ra (SEQ ID NO:6) were used in place of the anti-tag antibodies. In these studies with murine mast cells, the results again demonstrated that CD200Ra is an inhibitory receptor.

Monoclonal antibodies specific for human CD200Ra were tested for agonist activity using activated mast cells. Anti-huCD200Ra antibodies, i.e., DX136 (rIgG2a) and DX139 (rIgM), were found to be agonists of CD200Ra as measured by assessing changes in degranulation and secretion, using murine mast cells expressing human CD200Ra. Agonist activity is expressed by IC50.

Fusion proteins, comprising two CD200 extracellular domains fused to an Fc region, were also tested for agonist activity (huCD200-Ig; muCD200-Ig). These fusion proteins contained a mutation (D265A in the constant regions of the Fc used to create both huCD200-Ig and muCD200-Ig) to prevent binding to Fc receptor (FcR) and to complement (Idusogie, et al. (2000) *J. Immunol.* 164:4178-4184). These fusion proteins also delivered a signal that inhibited mast cell degranulation and cytokine secretion.

FACS analysis of blood cells revealed the types of white blood cells expressing CD200R, where cells were tagged by the indicated antibody (Table 2). Receptor internalization was measured by confocal microscopy (Liu, et al. (1998) *Cancer Res.* 58:4055-4060; Lee, et al. (2000) *J. Pharmacol. Exp. Therapeutics* 292:1048-1052) (Table 2). ND means not determined. Immunohistochemistry (IHC) refers to the ability of the indicated mAb to stain cells in frozen, acetone-fixed, human or mouse tissue, or formalin-fixed, paraffin-embedded human or mouse tissues.

The results demonstrated that treatment with each of the anti-CD200R antibodies and with the CD200-Ig fusion protein inhibited mast cell degranulation. Control isotype antibodies did not detectably influence secretion. However, each of the tested compounds inhibited with differing efficiencies, as determined by the IC50 (Table 2). In addition to having a better agonistic effect, the antibodies' effect was also longer lasting than that of the Ig-fusion protein.

Figure 2:
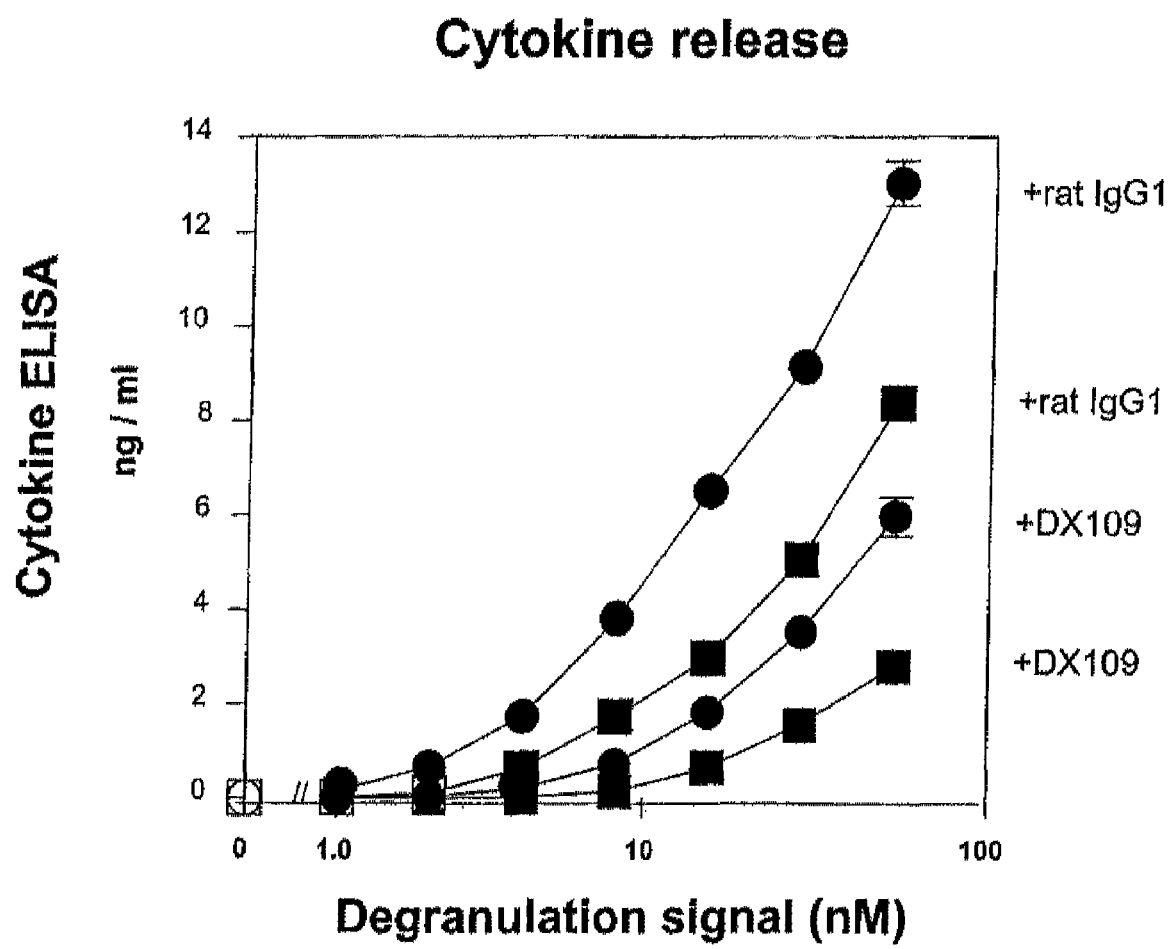
FIG. 2 shows cytokine release versus concentration of degranulation signal.

Mouse mast cells were stimulated with IgE anti-TNP with antigen (TNP-keyhole limpet hemocyanin; KLH), followed by assay of released β-hexosaminidase (degranulation; $Abs_{405-650}$) and cytokine (secretion) (FIGS. 1-2) The degranulation signal, IgE anti-TNP, was used at the indicated concentrations. DX109 monoclonal anti-CD200R antibody (mAb) and control rat IgG I mAb were tested for their effect on inhibiting mast cell activity. DX109 mAb or rat IgG1 mAb were added at a constant concentration of 13 nm. The cytokines assayed were IL-13 and tumor necrosis factor (TNF) (FIGS. 1-2). Degranulation, as assessed by hexosaminidase release, was studied (FIG. 1). Increases in stimulant concen-

TABLE 2

| Name | Species and isotype | Agonist activity | Bioassay IC50 | FACS analysis of blood | IHC | Receptor internalization |
|---|---|---|---|---|---|---|
| Agonists of human CD200Ra (SEQ ID NO: 2) | | | | | | |
| DX136 | Rat IgG2a | Yes | 1.0 nM | T cells+<br>Monocytes+<br>Neutrophils+++<br>Basophils++ | Yes | No |
| DX138 | Rat IgG2a | Yes | 40 nM | T cells+<br>Monocytes+<br>Neutrophils+++<br>Basophils++ | Yes | Yes |
| DX139 | Rat IgM | Strong | 0.01 nM | T cells+<br>Neutrophils+++<br>Basophils+ | Yes | No |
| DX142 | Rat IgG1 | Yes | 0.5 nM | Neutrophils+ | No | ND |
| DX147 | Rat IgG1 | Yes | 0.2 nM | Neutrophils+ | Yes | No |
| DX153 | Rat IgG1 | Yes | 0.14 nM | T cells(+, −);<br>monocytes (+);<br>neutrophils (+++);<br>basophils (+) | | |
| huCD200-Ig | Mouse IgG1 | Yes | 0.3 nM | ND | ND | ND |
| Agonists of mouse CD200Ra (SEQ ID NO: 6) | | | | | | |
| DX109 | Rat IgG1 | yes | 0.2 nM | T cells+<br>Monocytes++<br>Neutrophils+++ | Yes | No |
| DX110 | Rat IgG1 | yes, less than DX109 | ND | ND | Yes | ND |
| muCD200-Ig | Mouse IgG1 | yes | 1.3 nM | ND | ND | ND |

Mouse mast cells expressing the human CD200Ra molecule were stimulated with 25 µg/ml monoclonal antibody to trigger the Dap12-linked activating receptor of mouse CD200Rd, followed by measurement of secreted β-hexosaminidase at 1.0 hours (Table 2). Agonist activity of anti-CD200Ra antibody or CD200-Ig fusion protein was assessed by adding anti-CD200Ra antibody or CD200-Ig fusion protein to the cell incubation mixtures and determining inhibition of secretion. Incubations were conducted with antibodies or CD200-Ig fusion protein at concentrations of 0, 0.01, 0.03, 0.1, 0.3, 1.0, 3.0, and 9.0 µg/ml. Control cell incubations were conducted with the rat isotype control mAb.

tration were followed by increases in hexosaminidase release where control rat IgG1 was added (upper curve, closed squares, FIG. 1), while incubations containing added DX109 mAb had relatively low levels of hexosaminidase release, except at the highest level of stimulant (lower curve, closed triangles, FIG. 1). Increasing stimulant concentration resulted in increases in secretion of IL-13 (closed circles, FIG. 2) and TNF (closed squares, FIG. 2) where secretion of both cytokines was inhibited by DX109 monoclonal antibody. The results demonstrate that anti-CD200R antibody is effective in inhibiting degranulation and cytokine secretion.

VI. Cross-Linking an Inhibiting Receptor with an Activating Receptor

Degranulation and secretion by human mast cells was measured by a protocol involving addition of anti-IgE receptor antibody, which binds to IgE receptor, addition of anti-CD200R antibody, which binds to CD200Ra (SEQ ID NO:2), and addition of goat anti-mouse F(ab')$_2$, which binds simultaneously to the anti-IgE antibody (adhering to IgE receptor) and to anti-CD200R antibody (adhering to CD200R). Control experiments involved variations of this protocol.

Whole cord blood cells were cultured in Yssels medium supplemented with stem cell factor (SCF) and IL-6 for 4-6 weeks to produce human mast cells. IL-4 and IgE were added to the culture for an additional 2 weeks. Cells were then plated at $10^6$ cells/well in 96 well flat bottom plates. An inhibitory antibody (anti-CD200Ra antibody) or control antibody (mouse Ig) was then added. After 20 min incubation, anti-IgE receptor antibody was added to a concentration of 20 ng/ml. After 20 min of further incubation, the wells were washed and the crosslinker (goat anti-mouse antibody) was added. The mixture was incubated for 1 h, and the supernatant withdrawn and used for degranulation assays, as assessed by tryptase release. Tryptase assays were performed with the substrate N-alpha-benzyl-DL-arginine p-nitroanilide hydrochloride (BAPNA) with color measurement at 405-570 nm.

Degranulation (tryptase release) was maximal with addition of anti-IgE receptor antibody and control antibody (mouse Ig). Maximal tryptase release, under these conditions, resulted in $Abs_{405-570}$=0.44-0.51. In incubations with anti-CD200Ra antibody, titrating levels of anti-CD200Ra antibody were used (0-1000 ng/ml anti-CD200Ra antibody). Different levels of antibody were used in separate incubation mixtures. Anti-CD200Ra antibody at increasing levels resulted in the progressive inhibition of tryptase release, where maximal inhibition ($Abs_{405-570}$=0.05) occurred with about 1000 ng/ml anti-CD200Ra antibody. Intermediate levels of anti-CD200Ra antibody (200 ng/ml) inhibited tryptase release to about 25% the level of maximal tryptase release. The results demonstrate that cross-linking CD200Ra with IgE receptor prevents IgE receptor-dependent degranulation in human mast cells.

Cross-linking of various inhibitory receptors, other than CD200Ra (SEQ ID NO:2), with FceRI also inhibited mast cell activity. The inhibitory receptors studied were DSP-1 and LAIR-1. Anti-DSP-1 antibody or anti-LAIR-1 antibody were used as agonists for DSP-1 or LAIR-1, respectively. Degranulation (tryptase release) was maximal with addition of anti-IgE receptor antibody plus control antibody (mouse Ig). Maximal tryptase release, under these conditions, resulted in $Abs_{405-570}$=0.44-0.51. Titrating levels of anti-DSP-1 antibody were used (0-1000 ng/ml anti-DSP-1 antibody), with different levels of anti-DSP-1 antibody in separate incubation mixtures. Increasing concentrations of anti-DSP-1 antibody resulted in progressive inhibition of tryptase release, where maximal inhibition ($Abs_{405-570}$=0.08) occurred at about 40 ng/ml anti-DSP-1 antibody, as well as at higher concentrations of anti-DSP-1 antibody. Intermediate concentrations of anti-DSP-1 antibody (about 8 ng/ml) resulted in 25% maximal tryptase release. The results demonstrate that cross-linking DSP-1 with IgE receptor prevents IgE receptor-dependent degranulation.

In studies involving the inhibitory receptor LAIR-1, anti-LAIR-1 antibody was used at 0 or 50 ng/ml. Where incubations contained only activating antibody (anti-IgE receptor antibody), tryptase release was about $Abs_{405-570}$=0.69 (defined as maximal). Where incubations contained activating antibody (anti-IgE receptor), anti-LAIR-1 antibody (50 ng/ml), and cross-linker, tryptase release was inhibited, and where tryptase release at the inhibited level was about 10% maximal ($Abs_{405-570}$=0.07). Control incubations containing no activating antibody resulted in very little tryptase release ($Abs_{450-570}$=0.06). The results demonstrate that cross-linking LAIR-1 with IgE receptor prevents IgE receptor-dependent degranulation.

VII. Preventing Mast Cell Degranulation In Vivo

To determine if agonism of the CD200Ra molecule could also prevent mast cell degranulation in vivo, the passive cutaneous anaphylaxis (PCA) was employed. Each mouse in a group of five 30 g CD1 mice was injected i.v. with 100 µg of DX109 (rat anti-muCD200Ra mAb). Each mouse in a second group of five, 30 g CD1 mice was injected i.v. with 100 µg of rat IgG1 control mAb. One hour later, the backs of all ten mice were shaved and mouse IgE anti-DNP mAb was injected intradermally (i.d.) in a volume of 20 µl at 3 sites per mouse, respectively 10, 20 or 40 ng IgE per site. Twenty four hours later, all mice received i.v. a mixture of antigen (DNP-HSA) and the dye Evans's blue. Where the injected antigen binds to, and cross-links the IgE bound to skin mast cells, degranulation occurs, leading to release of mediators such as histamine that cause vascular edema, enabling the movement of the blue dye from the blood into the skin and appearance of blue spots on the skin. The size of the blue spot is proportional to the amount of IgE injected into the skin at that site. In mice receiving 100 µg of the control IgG1 mAb, the PCA reaction proceeded and blue spots appeared in all five mice, the largest size spot at the site where 40 ng IgE was injected, the smallest blue spot where 10 ng IgE was injected. In mice receiving the DX109 anti-CD200Ra mAb, no blue spots appeared at any concentration of injected IgE. Thus, as in the in vitro studies; the DX109 mAb delivered an inhibitory signal to the skin mast cells in vivo, preventing degranulation.

VIII. Treatment of Collagen Induced Arthritis (CIA) with Anti-CD200Ra Antibody CIA was induced in mice followed by treatment with anti-CD200Ra antibody (DX109 mAb) or with control IgG antibody. Female B10.RIII mice, 8-10 weeks old, were treated with bovine type II collagen in complete Freund's adjuvant (CFA) (Jirholt, et al. (1998) *Eur. J. Immunol.* 28:3321-3328). At day 0, mice were treated with one dose of bovine Type II collagen in CFA. Starting at day 7, antibody was administered at weekly intervals. DX109 antibody and control IgG doses were 1 mg, i.p. at days 7 and 14, and 1 mg, s.c. at days 21 and 28. Disease scoring commenced at day 14 and was continued to day 45. Experimental mice received DX109, while control mice received control IgG.

CIA was scored by cumulative incidence in units of percent. The control group showed 0% score from t=14-18 days; 40% score at t=19-20 days; 60% score at t=21-30 days; and 80% score at t=31-44 days. The DX109-treated group showed 0% score from t=14-24 days and 20% score from t=25-44 days. Thus DX109-treatment resulted in lower scores and relief from CIA.

CIA was also scored by Mean Clinical Score (MCS) (Hoek, et al, supra). The control group showed a MCS=0 at 14-19 days; MCS=1 at 20-21 days; MCS=~2 at 22-31 days, followed by a progressive increase to MCS=~4.5, where a score of MCS=~4.5 occurred at days 39-44. The DX109-treated group showed MCS=0 at 14-24 days, MCS=0.2 at 25-26 days, MCS=0.5 at 27-34 days, MCS=0.2 at 35-42 days, and MCS=0.5 at 43-44 days. Again, the results demonstrated that DX109-treatment resulted in lower scores and relief from CIA.

IX. Effects of Anti-CD200R Antibody on LPS-Induced Endotoxaemia

Endotoxaemia was induced in mice by LPS-treatment followed by treatment with anti-CD200R antibody (DX109) or control antibody and assessment of survival rate. The LPS dose was adjusted to provide sufficient toxicity to provoke toxicity and death of the mice, while avoiding saturating levels that would prevent the antibody from enhancing survival. The mice were of the C57BL/6 strain. Mice received 0.5 mg antibody (i.p.) at two time points, i.e., 1 hour prior to as well as simultaneously with the LPS. The anti-CD200R antibody treated mice showed a higher survival rate at various time points when compared to the control group. The results demonstrated that anti-CD200R antibody protects mice from LPS-induced toxicity.

X. Distribution of CD200Ra in Human Skin

CD200Ra was visualized in green by rat anti-CD200Ra and tagging with goat anti-rat containing Alexa Fluor®-488 (Molecular Probes, Eugene, Oreg.). Mast cells were visualized in red with mouse anti-CD117 (a marker for mast cells) and tagging with goat anti-mouse containing Alexa Fluor®-594 (Molecular Probes, Eugene, Oreg.). Staining with anti-CD117 revealed an array of discrete red spots. Staining with both antibodies indicated that about one third of CD200Ra-bearing cells were mast cells.

Normal human skin was also tested for localization of CD200Ra (SEQ ID NO:2) on macrophages. CD200Ra was localized by staining with anti-CD200Ra tagged with green. Macrophages were located with anti-CD11b antibody tagged with red. Staining with either antibody alone or with both antibodies together demonstrated that a majority of macrophages expressed CD200Ra.

Normal human and psoriatic skin was probed with anti-CD200Ra (DX136), stained with horse radish peroxidase (HRP), and examined under visible light. The results showed that psoriatic skin was profusely stained in both the dermis and epidermis, when compared to normal skin. The psoriatic skin contained large clusters of CD200Ra$^+$ cells, where these cells appeared to consist of T cells and myeloid cells.

SEQUENCE IDENTIFIERS

SEQ ID NO:1 is human CD200Ra nucleic acid.
SEQ ID NO:2 is human CD200Ra polypeptide.
SEQ ID NO:3 is human CD200RB nucleic acid.
SEQ ID NO:4 is human CD200Rb polypeptide.
SEQ ID NO:5 is murine CD200Ra nucleic acid.
SEQ ID NO:6 is murine CD200Ra polypeptide.
SEQ ID NO:7 is murine CD200Rb nucleic acid.
SEQ ID NO:8 is murine CD200Rb polypeptide.
SEQ ID NO:9 is murine CD200Rc nucleic acid.
SEQ ID NO:10 is murine CD200Rc polypeptide.
SEQ ID NO:11 is murine CD200Rd nucleic acid.
SEQ ID NO:12 is murine CD200Rd polypeptide.
SEQ ID NO:13 is rat CD200R nucleic acid.
SEQ ID NO:14 is rat CD200R polypeptide.

All citations herein are incorporated herein by reference to the same extent as if each individual publication, patent application, or patent was specifically and individually indicated to be incorporated by reference including all figures and drawings.

Many modifications and variations of this invention, as will be apparent to one of ordinary skill in the art, can be made to adapt to a particular situation, material, composition of matter, process, process step or steps, to preserve the objective, spirit, and scope of the invention. All such modifications are intended to be within the scope of the claims appended hereto without departing from the spirit and scope of the invention. The specific embodiments described herein are offered by way of example only, and the invention is to be limited by the terms of the appended claims, along with the full scope of the equivalents to which such claims are entitled; and the invention is not to be limited by the specific embodiments that have been presented herein by way of example.

What is claimed is:

1. A method of treating allergic rhinitis comprising, contacting a mast cell with an agonist antibody that specifically binds to CD200Ra (SEQ ID NO:2) or an antigenic fragment of CD200Ra (SEQ ID NO:2), wherein said agonist antibody inhibits degranulation by the mast cell.

2. The method of claim 1, wherein the antibody is selected from the group consisting of a humanized antibody, a monoclonal antibody and a polyclonal antibody.

3. The method of claim 2, wherein the antibody is a humanized antibody.

4. The method of claim 1, further comprising administering a second agent.

5. The method of claim 4, wherein the second agent is selected from the group consisting of an immunosuppressive agent and an anti-inflammatory agent.

6. The method of claim 5, wherein the second agent is an anti-inflammatory agent.

7. The method of claim 6, wherein the anti-inflammatory agent is a steroid.

* * * * *